United States Patent
Huang et al.

(10) Patent No.: US 10,876,997 B2
(45) Date of Patent: Dec. 29, 2020

(54) BIO-FIELD EFFECT TRANSISTOR DEVICE

(71) Applicant: Taiwan Semiconductor Manufacturing Co., Ltd., Hsinchu (TW)

(72) Inventors: Jui-Cheng Huang, Hsinchu (TW); Yi-Hsien Chang, Changhua County (TW); Chin-Hua Wen, Miaoli County (TW); Chun-Ren Cheng, Hsinchu (TW); Shih-Fen Huang, Jhubei (TW); Tung-Tsun Chen, Hsinchu (TW); Yu-Jie Huang, Kaohsiung (TW); Ching-Hui Lin, Taichung (TW); Sean Cheng, Hsinchu (TW); Hector Chang, Hsinchu (TW)

(73) Assignee: Taiwan Semiconductor Manufacturing Co., Ltd.

( * ) Notice: Subject to any disclaimer, the term of this patent is extended or adjusted under 35 U.S.C. 154(b) by 378 days.

(21) Appl. No.: 15/661,969

(22) Filed: Jul. 27, 2017

(65) Prior Publication Data

US 2019/0033252 A1    Jan. 31, 2019

(51) Int. Cl.
*G01N 27/414* (2006.01)
*H01L 41/09* (2006.01)
(Continued)

(52) U.S. Cl.
CPC ...... *G01N 27/4145* (2013.01); *B01F 11/0258* (2013.01); *B01F 13/0059* (2013.01);
(Continued)

(58) Field of Classification Search
CPC ........................................ G01N 27/414–4148; G01N 33/54366–54386; B01F 11/0258;
(Continued)

(56) References Cited

U.S. PATENT DOCUMENTS 7,015,090 B2    3/2006  Okazaki et al.
2004/0077116 A1*  4/2004  Hsiung ............... H01L 27/144
                                                                  438/48
(Continued)

FOREIGN PATENT DOCUMENTS

CN          1622311 A       6/2005
DE    10 2016 125 295 A1   6/2018
(Continued)

OTHER PUBLICATIONS

Meldrum, Deirdre, et al. "MEMS modules for life-on-a-chip." Proceedings of the 2003 International Symposium on Circuits and Systems, 2003. ISCAS'03.. vol. 3. IEEE, 2003.*

*Primary Examiner* — Robert J Eom
(74) *Attorney, Agent, or Firm* — Sterne, Kessler, Goldstein & Fox P.L.L.C.

(57) ABSTRACT

A bioFET device includes a semiconductor substrate having a first surface and an opposite, parallel second surface and a plurality of bioFET sensors on the semiconductor substrate. Each of the bioFET sensors includes a gate formed on the first surface of the semiconductor substrate and a channel region formed within the semiconductor substrate beneath the gate and between source/drain (S/D) regions in the semiconductor substrate. The channel region includes a portion of the second surface of the semiconductor substrate. An isolation layer is disposed on the second surface of the semiconductor substrate. The isolation layer has an opening positioned over the channel region of more than one bioFET sensor of the plurality of bioFET sensors. An interface layer is disposed on the channel region of the more than one bioFET sensor in the opening.

30 Claims, 23 Drawing Sheets

(51) Int. Cl.
    *B01L 3/00*     (2006.01)
    *B01F 11/02*     (2006.01)
    *B01F 13/00*     (2006.01)
    *G01N 33/543*     (2006.01)
    *H01L 41/08*     (2006.01)
    *C12Q 1/6825*     (2018.01)

(52) U.S. Cl.
    CPC .... B01F 13/0096 (2013.01); B01L 3/502707 (2013.01); B01L 3/502715 (2013.01); B01L 3/502761 (2013.01); B01L 3/502792 (2013.01); G01N 33/5438 (2013.01); H01L 41/0805 (2013.01); H01L 41/094 (2013.01); H01L 41/0973 (2013.01); *B01L 2200/12* (2013.01); *B01L 2300/06* (2013.01); *B01L 2300/0645* (2013.01); *B01L 2300/0663* (2013.01); *B01L 2300/0819* (2013.01); *B01L 2300/0887* (2013.01); *B01L 2300/1827* (2013.01); *C12Q 1/6825* (2013.01)

(58) Field of Classification Search
    CPC ........... B01F 13/0096; B01L 3/502707; B01L 3/502715; B01L 3/502761; B01L 3/502792; H01L 41/0805; H01L 41/094; H01L 41/0973

See application file for complete search history.

(56) References Cited

U.S. PATENT DOCUMENTS

| | | | |
|---|---|---|---|
| 2013/0105868 | A1 | 5/2013 | Kalnitsky et al. |
| 2013/0143221 | A1* | 6/2013 | Beauchemin ...... G01N 27/4145 435/6.12 |
| 2013/0200438 | A1* | 8/2013 | Liu ................... H01L 29/66477 257/253 |
| 2017/0016851 | A1 | 1/2017 | Cheng et al. |
| 2017/0160226 | A1 | 6/2017 | Huang et al. |
| 2017/0205371 | A1 | 7/2017 | Liu et al. |
| 2018/0164246 | A1 | 6/2018 | Chen et al. |

FOREIGN PATENT DOCUMENTS

| | | |
|---|---|---|
| KR | 10-2011-0037283 | 4/2011 |
| KR | 10-2017-0067122 | 6/2017 |

* cited by examiner

BIO-FIELD EFFECT TRANSISTOR DEVICE

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs) and microelectromechanical systems (MEMS).

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
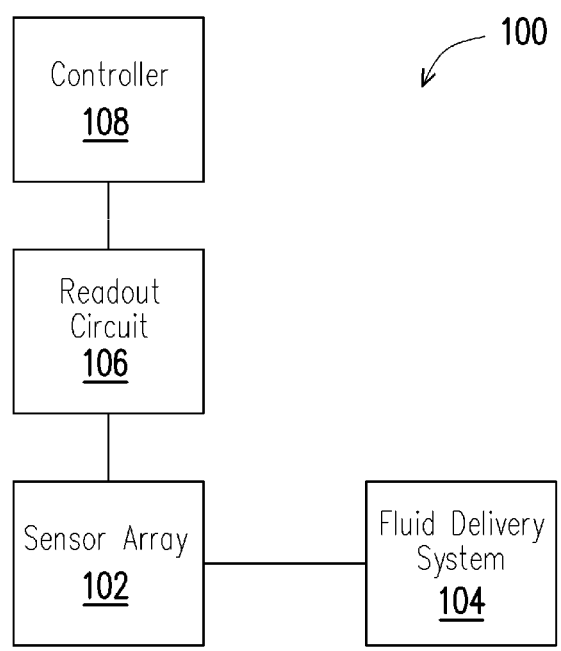
FIG. 1 illustrates components of a sensing device, according to some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over a second feature in the description that follows may include embodiments in which the first and second features are formed in direct contact, and may also include embodiments in which additional features may be formed and/or disposed between the first and second features, such that the first and second features may not be in direct contact. In addition, the present disclosure may repeat reference numerals and/or letters in the various examples. This does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (e.g., rotated 90 degrees or at other orientations) and the spatially relative descriptors used herein may likewise be interpreted accordingly.

Terminology

Unless defined otherwise, the technical and scientific terms used herein have the same meanings as commonly understood by one of ordinary skill in the art to which this disclosure belongs. Although any methods and materials similar or equivalent to those described herein can be used in the practice or testing of embodiments in accordance with the disclosure; the methods, devices, and materials are now described. All patents and publications mentioned herein are incorporated herein by reference for the purpose of describing and disclosing the materials and methodologies which are reported in the publications which might be used in connection with the present disclosure.

The acronym "FET," as used herein, refers to a field effect transistor. An example of a type of FET is referred to as a metal oxide semiconductor field effect transistor (MOSFET). Historically, MOSFETs have been planar structures built in and on the planar surface of a substrate such as a semiconductor wafer. But recent advances in semiconductor manufacturing have resulted in three-dimensional, fin-based MOSFET structures.

The term "bioFET" refers to a FET that includes a layer of immobilized capture reagents that act as surface receptors to detect the presence of a target analyte of biological origin. A bioFET is a field-effect sensor with a semiconductor transducer, according to some embodiments. One advantage of bioFETs is the prospect of label-free operation. Specifically, bioFETs enable the avoidance of costly and time-consuming labeling operations such as the labeling of an analyte with, for instance, fluorescent or radioactive probes. The analytes for detection by a bioFET will normally be of biological origin, such as—without limitation—proteins, carbohydrates, lipids, tissue fragments, or portions thereof. A BioFET can be part of a broader genus of FET sensors that may also detect any chemical compound (known in the art as a "ChemFET") or any other element, including ions such as protons or metallic ions (known in the art as an "ISFET"). This disclosure applies to all types of FET-based sensors ("FET sensor"). One specific type of FET sensor herein is a Dual-Gate Back Side Sensing FET Sensor.

"S/D" refers to the source/drain junctions that form two of the four terminals of a FET.

The expression "high-k" refers to a high dielectric constant. In the field of semiconductor device structures and manufacturing processes, high-k refers to a dielectric constant that is greater than the dielectric constant of $SiO_2$ (i.e., greater than 3.9).

The term "analysis" generally refers to a process or step involving physical, chemical, biochemical, or biological analysis that includes, but is not limited to, characterization, testing, measurement, optimization, separation, synthesis, addition, filtration, dissolution, or mixing.

The term "assay" generally refers to a process or step involving the analysis of a chemical or a target analyte and includes, but is not limited to, cell-based assays, biochemical assays, high-throughput assays and screening, diagnostic assays, pH determination, nucleic acid hybridization assays, polymerase activity assays, nucleic acid and protein sequencing, immunoassays (e.g., antibody-antigen binding assays, enzyme-linked immunosorbent assays (ELISAs), and immunoquantitative polymerase chain reaction (iqPCR)), bisulfite methylation assays for detecting methylation pattern of genes, protein assays, protein binding assays (e.g., protein-protein, protein-nucleic acid, and protein-ligand binding assays), enzymatic assays, coupled enzymatic assays, kinetic measurements (e.g., kinetics of protein folding and enzymatic reaction kinetics), enzyme inhibitor and activator screening, chemiluminescence and electrochemiluminescence assays, fluorescent assays, fluorescence polarization and anisotropy assays, absorbance and colorimetric assays (e.g., Bradford assay, Lowry assay, Hartree-Lowry assay, Biuret assay, and bicinchoninic acid (BCA) assay), chemical assays (e.g., for the detection of environmental pollutants and contaminants, nanoparticles, or polymers), and drug discovery assays. The apparatus, systems, and methods described herein may use or adopt one or more of these assays to be used with the FET sensor designs described herein.

The term "liquid biopsy" generally refers to a biopsy sample obtained from a subject's bodily fluid as compared to a subject's tissue sample. The ability to perform assays using a body fluid sample is oftentimes more desirable than using a tissue sample. The less invasive approach using a body fluid sample has wide ranging implications in terms of patient welfare, the ability to conduct longitudinal disease monitoring, and the ability to obtain expression profiles even when tissue cells are not easily accessible, for example, in the prostate gland. Assays used to detect target analytes in liquid biopsy samples include, but are not limited to, those described above. As a non-limiting example, a circulating tumor cell (CTC) assay can be conducted on a liquid biopsy sample.

For example, a capture reagent (e.g., an antibody) immobilized on a FET sensor may be used for detection of a target analyte (e.g., a tumor cell marker) in a liquid biopsy sample using a CTC assay. CTCs are cells that have shed into the vasculature from a tumor and circulate, for example, in the bloodstream. Generally, CTCs are present in circulation in extremely low concentrations. To assay the CTCs, CTCs are enriched from patient blood or plasma by various techniques known in the art. CTCs may be stained for specific markers using methods known in the art including, but not limited to, cytometry (e.g., flow cytometry)-based methods and immunohistochemistry (IHC)-based methods. For the apparatus, systems, and methods described herein, CTCs may be captured or detected using a capture reagent. In another example, the nucleic acids, proteins, or other cellular milieu from the CTCs may be targeted as target analytes for binding to, or detection by, a capture reagent.

An increase in target analyte expressing or containing CTCs may help identify the subject as having a cancer that is likely to respond to a specific therapy (e.g., one associated with the target analyte) or allow for optimization of a therapeutic regimen with, for example, an antibody to the target analyte. CTC measurement and quantitation can provide information on, for example, the stage of tumor, response to therapy, disease progression, or a combination thereof. The information obtained from detecting the target analyte on the CTC can be used, for example, as a prognostic, predictive, or pharmacodynamic biomarker. In addition, CTCs assays for a liquid biopsy sample may be used either alone or in combination with additional tumor marker analysis of solid biopsy samples.

The term "identification" generally refers to the process of determining the identity of a target analyte based on its binding to a capture reagent whose identity is known.

The term "measurement" generally refers to the process of determining the amount, quantity, quality, or property of a target analyte based on its binding to a capture reagent.

The term "quantitation" generally refers to the process of determining the quantity or concentration of a target analyte based on its binding to a capture reagent.

The term "detection" generally refers to the process of determining the presence or absence of a target analyte based on its binding to a capture reagent. Detection includes, but is not limited to, identification, measurement, and quantitation.

The term "chemical" refers to a substance, compound, mixture, solution, emulsion, dispersion, molecule, ion, dimer, macromolecule such as a polymer or protein, biomolecule, precipitate, crystal, chemical moiety or group, particle, nanoparticle, reagent, reaction product, solvent, or fluid any one of which may exist in the solid, liquid, or gaseous state, and which is typically the subject of an analysis.

The term "reaction" refers to a physical, chemical, biochemical, or biological transformation that involves at least one chemical and that generally involves (e.g., in the case of chemical, biochemical, and biological transformations) the breaking or formation of one or more bonds such as covalent, noncovalent, van der Waals, hydrogen, or ionic bonds. The term "reaction" includes chemical reactions such as synthesis reactions, neutralization reactions, decomposition reactions, displacement reactions, reduction-oxidation reactions, precipitation, crystallization, combustion reactions, and polymerization reactions, as well as covalent and non-covalent binding, phase change, color change, phase formation, dissolution, light emission, changes of light absorption or emissive properties, temperature change or heat absorption or emission, conformational change, and folding or unfolding of a macromolecule such as a protein.

"Capture reagent," as used herein, is a molecule or compound capable of binding the target analyte or target reagent, which can be directly or indirectly attached to a substantially solid material. The capture agent can be a chemical, and specifically any substance for which there exists a naturally occurring target analyte (e.g., an antibody, polypeptide, DNA, RNA, cell, virus, etc.) or for which a target analyte can be prepared, and the capture reagent can bind to one or more target analytes in an assay.

"Target analyte," as used herein, is the substance to be detected in the test sample using the present disclosure. The target analyte can be a chemical, and specifically any substance for which there exists a naturally occurring capture reagent (e.g., an antibody, polypeptide, DNA, RNA, cell, virus, etc.) or for which a capture reagent can be prepared, and the target analyte can bind to one or more capture reagents in an assay. "Target analyte" also includes any antigenic substances, antibodies, or combinations thereof. The target analyte can include a protein, a peptide, an amino acid, a carbohydrate, a hormone, a steroid, a vitamin, a drug including those administered for therapeutic purposes as well as those administered for illicit purposes, a bacterium, a virus, and metabolites of or antibodies to any of the above substances.

"Test sample," as used herein, means the composition, solution, substance, gas, or liquid containing the target analyte to be detected and assayed using the present disclosure. The test sample can contain other components besides the target analyte, can have the physical attributes of a liquid, or a gas, and can be of any size or volume, including for example, a moving stream of liquid or gas. The test sample can contain any substances other than the target analyte as long as the other substances do not interfere with the binding of the target analyte with the capture reagent or the specific binding of the first binding member to the second binding member. Examples of test samples include, but are not limited to, naturally-occurring and non-naturally occurring samples or combinations thereof. Naturally-occurring test samples can be synthetic or synthesized. Naturally-occurring test samples include body or bodily fluids isolated from anywhere in or on the body of a subject, including, but not limited to, blood, plasma, serum, urine, saliva or sputum, spinal fluid, cerebrospinal fluid, pleural fluid, nipple aspirates, lymph fluid, fluid of the respiratory, intestinal, and genitourinary tracts, tear fluid, breast milk, fluid from the lymphatic system, semen, intra-organ system fluid, ascitic fluid, tumor cyst fluid, amniotic fluid and combinations thereof, and environmental samples such as ground water or waste water, soil extracts, air, and pesticide residues or food-related samples.

Detected substances can include, for example, nucleic acids (including DNA and RNA), hormones, different pathogens (including a biological agent that causes disease or illness to its host, such as a virus (e.g., H7N9 or HIV), a protozoan (e.g., *Plasmodium*-causing malaria), or a bacteria (e.g., *E. coli* or *Mycobacterium tuberculosis*)), proteins, antibodies, various drugs or therapeutics or other chemical or biological substances, including hydrogen or other ions, non-ionic molecules or compounds, polysaccharides, small chemical compounds such as chemical combinatorial library members, and the like. Detected or determined parameters may include, but are not limited to, pH changes, lactose changes, changing concentration, particles per unit time where a fluid flows over the device for a period of time to detect particles (e.g., particles that are sparse), and other parameters.

As used herein, the term "immobilized," when used with respect to, for example, a capture reagent, includes substantially attaching the capture reagent at a molecular level to a surface. For example, a capture reagent may be immobilized to a surface of the substrate material using adsorption techniques including non-covalent interactions (e.g., electrostatic forces, van der Waals, and dehydration of hydrophobic interfaces) and covalent binding techniques where functional groups or linkers facilitate attaching the capture reagent to the surface. Immobilizing a capture reagent to a surface of a substrate material may be based on the properties of the substrate surface, the medium carrying the capture reagent, and the properties of the capture reagent. In some cases, a substrate surface may be first modified to have functional groups bound to the surface. The functional groups may then bind to biomolecules or biological or chemical substances to immobilize them thereon.

The term "nucleic acid" generally refers to a set of nucleotides connected to each other via phosphodiester bond and refers to a naturally occurring nucleic acid to which a naturally occurring nucleotide existing in nature is connected, such as DNA that includes deoxyribonucleotides having any of adenine, guanine, cytosine, and thymine connected to each other and/or RNA that includes ribonucleotides having any of adenine, guanine, cytosine, and uracil connected to each other. In addition, non-naturally occurring nucleotides and non-naturally occurring nucleic acids are within the scope of the nucleic acid of the present disclosure. Examples include peptide nucleic acids (PNA), peptide nucleic acids with phosphate groups (PHONA), bridged nucleic acids/locked nucleic acids (BNA/LNA), and morpholino nucleic acids. Further examples include chemically-modified nucleic acids and nucleic acid analogues, such as methylphosphonate DNA/RNA, phosphorothioate DNA/RNA, phosphoramidate DNA/RNA, and 2'-O-methyl DNA/RNA. Nucleic acids include those that may be modified. For example, a phosphoric acid group, a sugar, and/or a base in a nucleic acid may be labeled as necessary. Any substance for nucleic acid labeling known in the art can be used for labeling. Examples thereof include, but are not limited to, radioactive isotopes (e.g., 32P, 3H, and 14C), DIG, biotin, fluorescent dyes (e.g., FITC, Texas, cy3, cy5, cy7, FAM, HEX, VIC, JOE, Rox, TET, Bodipy493, NBD, and TAMRA), and luminescent substances (e.g., acridinium ester).

The term "aptamer," as used herein, refers to oligonucleic acids or peptide molecules that bind to a specific target molecule. The concept of using single-stranded nucleic acids (aptamers) as affinity molecules for protein binding is based on the ability of short sequences to fold, in the presence of a target, into unique, three-dimensional structures that bind the target with high affinity and specificity. Aptamers can be oligonucleotide ligands selected for high-affinity binding to molecular targets.

The term "antibody" as used herein refers to a polypeptide of the immunoglobulin family that is capable of binding a corresponding antigen non-covalently, reversibly, and in a specific manner. For example, a naturally occurring IgG antibody is a tetramer that includes at least two heavy (H) chains and two light (L) chains inter-connected by disulfide bonds. Each heavy chain includes a heavy chain variable region (abbreviated herein as "VH") and a heavy chain constant region. The heavy chain constant region includes three domains: CH1, CH2, and CH3. Each light chain includes a light chain variable region (abbreviated herein as "VL") and a light chain constant region. The light chain constant region includes one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The three CDRs constitute about 15-20% of the variable domains. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antibody" includes, but is not limited to, monoclonal antibodies, human antibodies, humanized antibodies, chimeric antibodies, and anti-idiotypic (anti-Id) antibodies (including, e.g., anti-Id antibodies to antibodies of the present disclosure). The antibodies can be of any isotype/class (e.g., IgG, IgE, IgM, IgD, IgA, and IgY), or subclass (e.g., IgG1, IgG2, IgG3, IgG4, IgA1, and IgA2).

The term "polymer" means any substance or compound that is composed of two or more building blocks ('mers') that are repetitively linked to each other. For example, a "dimer" is a compound in which two building blocks have been joined together. Polymers include both condensation and addition polymers. Examples of condensation polymers include polyamide, polyester, protein, wool, silk, polyurethane, cellulose, and polysiloxane. Examples of addition polymers are polyethylene, polyisobutylene, polyacrylonitrile, poly(vinyl chloride), and polystyrene. Other examples include polymers having enhanced electrical or optical properties (e.g., a nonlinear optical property) such as electroconductive or photorefractive polymers. Polymers include both linear and branched polymers.

Overview of Exemplary Biosensing Device

FIG. 1 illustrates an overview of components that may be included in a biosensor system 100. Biosensor system 100 includes a sensor array 102 having at least one sensing element for detecting a biological or chemical analyte and a fluid delivery system 104 designed to deliver one or more fluid samples to sensor array 102. Fluid delivery system 104 may be a microfluidic well positioned above sensor array 102 to contain a fluid over sensor array 102. Fluid delivery system 104 may also include microfluidic channels for delivering various fluids to sensor array 102. Fluid delivery system 104 may include any number of valves, pumps, chambers, channels designed to deliver fluid to sensor array 102.

A readout circuit 106 is provided to measure signals from the sensors in sensor array 102 and to generate a quantifiable sensor signal indicative of the amount of a certain analyte that is present in a target solution, according to some embodiments. Different embodiments of readout circuit 106 described herein utilize digital components to reduce power consumption and die area.

A controller 108 may be used to send and receive electrical signals to both sensor array 102 and readout circuit 106 to perform bio- or chemical-sensing measurements. Controller 108 may also be used to send electrical signals to fluid delivery system 104 to, for example, actuate one or more valves, pumps, or motors.

Sensor array 102 may include an array of bioFETs, where one or more of the bioFETs in the array are functionalized to detect a particular target analyte. Different ones of the sensors may be functionalized using different capture reagents for detecting different target analytes. Further details regarding an example design of particular bioFETs are provided below. The bioFETs may be arranged in a plurality of rows and columns, forming a 2-dimensional array of sensors. In some embodiments, each row of bioFETs is functionalized using a different capture reagent. In some embodiments, each column of bioFETs is functionalized using a different capture reagent.

Controller 108 may include one or more processing devices, such as a microprocessor, and may be programmable to control the operation of readout circuit 106 and/or sensor array 102. The details of controller 108 itself are not important for the understanding of the embodiments described herein. However, the various electrical signals that may be sent and received from sensor array 102 will be discussed in more detail below.

Dual Gate Back-Side FET Sensors

Embodiments of the present application involve various layouts of bioFET sensors in sensor array 102 that allow for an opening to expose the channel regions of more than one bioFET sensor. Prior designs used separate openings over each bioFET sensor, which lead to some disadvantages as explained in more detail herein. This particular section describes an example bioFET sensor design that may be used in the embodiments of the present application.

One example type of bioFET sensor that may be used in sensor array 102 is the dual gate back-side FET sensor. Dual gate back-side FET sensors utilize semiconductor manufacturing techniques and biological capture reagents to form arrayed sensors. While MOSFETs can have a single gate electrode connected to a single electrical node, the dual gate back-side sensing FET sensor has two gate electrodes, each of which is connected to a different electrical node. A first one of the two gate electrodes is referred to herein as a "front-side gate," and the second one of the two gate electrodes is referred to herein as a "back-side gate." Both the front-side gate and the back-side gate are configured such that, in operation, each one may be electrically charged and/or discharged and thereby each influences the electric field between the source/drain terminals of the dual gate back-side sensing FET sensor. The front-side gate is electrically conductive, separated from a channel region by a front-side gate dielectric, and configured to be charged and discharged by an electrical circuit to which it is coupled. The back-side gate is separated from the channel region by a back-side gate dielectric and includes a bio-functionalized sensing layer disposed on the back-side gate dielectric. The amount of electric charge on the back-side gate is a function of whether a bio-recognition reaction has occurred. In the operation of dual gate back-side sensing FET sensors, the front-side gate is charged to a voltage within a predetermined range of voltages. The voltage on the front-side gate determines a corresponding conductivity of the FET sensor's channel region. A relatively small amount of change to the electric charge on the back-side gate changes the conductivity of the channel region. It is this change in conductivity that indicates a bio-recognition reaction.

One advantage of FET sensors is the prospect of label-free operation. Specifically, FET sensors enable the avoidance of costly and time-consuming labeling operations such as the labeling of an analyte with, for instance, fluorescent or radioactive probes.

Figure 2:
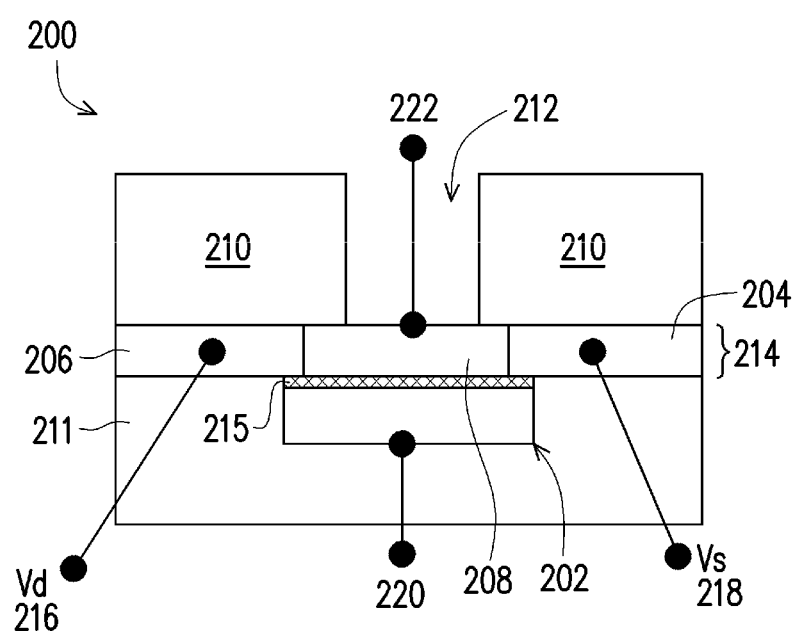
FIG. 2 illustrates a cross-sectional view of an exemplary dual-gate back-side sensing FET sensor, according to some embodiments.

FIG. 2 illustrates an exemplary dual gate back-side sensing FET sensor 200, according to some embodiments. Dual gate back-side sensing FET sensor 200 includes a control gate 202 formed on a surface of substrate 214 and separated therefrom by an intervening dielectric 215 disposed on substrate 214. An interconnect region 211 including a plurality of interconnect layers may be provided over one side of substrate 214. Substrate 214 includes a source region 204, a drain region 206, and a channel region 208 between source region 204 and drain region 206. In some embodiments, substrate 214 has a thickness between about 100 nm and about 130 nm. Gate 202, source region 204, drain region 206, and channel region 208 may be formed using suitable CMOS process technology. Gate 202, source region 204, drain region 206, and channel region 208 form a FET. An isolation layer 210 is disposed on the opposing side of substrate 214 from gate 202. In some embodiments, isolation layer 210 has a thickness of about 1 μm. In this disclosure the side of substrate 214 over which gate 202 is disposed is referred to as the "front-side" of substrate 214. Similarly, the side of substrate 214 on which isolation layer 210 is disposed is referred to as the "back-side."

An opening 212 is provided in isolation layer 210. Opening 212 may be substantially aligned with gate 202. In some embodiments, opening 212 is larger than gate 202 and may extend over multiple dual gate back-side sensing FET sensors. An interface layer (not shown) may be disposed in opening 212 on the surface of channel region 208. The interface layer may be operable to provide an interface for positioning and immobilizing one or more receptors for detection of biomolecules or bio-entities. Further details regarding the interface layer are provided herein.

Dual gate back-side sensing FET sensor 200 includes electrical contacts 216 and 218 to drain region 206 and source region 204, respectively. A front-side gate contact 220 may be made to gate 202, while a back-side gate contact 222 may be made to channel region 208. It should be noted that back-side gate contact 222 does not need to physically contact substrate 214 or any interface layer over substrate 214. Thus, while a FET can use a gate contact to control conductance of the semiconductor between the source and drain (e.g., the channel), dual gate back-side sensing FET sensor 200 allows receptors formed on a side opposing gate 202 of the FET device to control the conductance, while gate 202 provides another region to control the conductance. Therefore, dual gate back-side sensing FET sensor 200 may be used to detect one or more specific biomolecules or bio-entities in the environment around and/or in opening 212, as discussed in more detail using various examples herein.

Dual gate back-side sensing FET sensor 200 may be connected to: additional passive components such as resistors, capacitors, inductors, and/or fuses; other active components, including p-channel field effect transistors (PFETs), n-channel field effect transistors (NFETs), metal-oxide-semiconductor field effect transistors (MOSFETs), high voltage transistors, and/or high frequency transistors; other suitable components; or combinations thereof. It is further understood that additional features can be added in dual gate back-side sensing FET sensor 200, and some of the features described can be replaced or eliminated, for additional embodiments of dual gate back-side sensing FET sensor 200.

Figure 3:
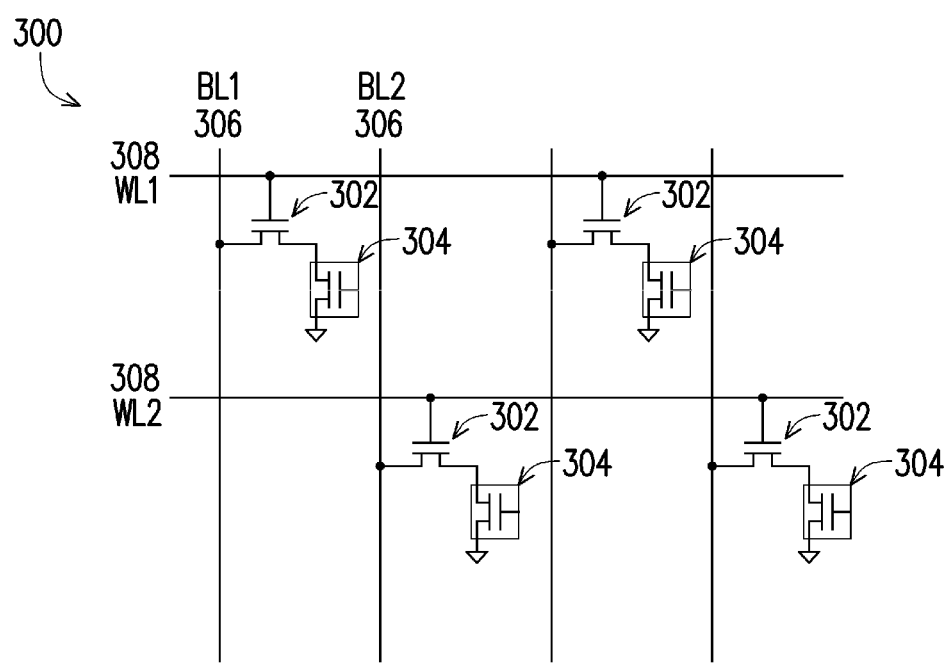
FIG. 3 is a circuit diagram of a plurality of FET sensors configured in an exemplary addressable array, according to some embodiments.

FIG. 3 illustrates a schematic of a portion of an exemplary addressable array 300 of bioFET sensors 304 connected to bit lines 306 and word lines 308. It is noted that the terms bit lines and word lines are used herein to indicate similarities to array construction in memory devices, however, there is no implication that memory devices or a storage array necessarily be included in the array. Addressable array 300 may have similarities to that employed in other semiconductor devices such as dynamic random access memory (DRAM) arrays. For example, dual gate back-side sensing FET sensor 200, described above with reference to FIG. 2, may be formed in a position that a capacitor would be found in a DRAM array. Schematic 300 is exemplary only and one would recognize other configurations are possible.

BioFET sensors 304 may each be substantially similar to dual gate back-side sensing FET sensor 200 according to some embodiments. FETs 302 are configured to provide an electrical connection between a drain terminal of bioFET sensor 304 and bit line 306. In this way, FETs 302 are analogous to access transistors in a DRAM array. In some embodiments, bioFET sensors 304 are dual gate back-side sensing FET sensors and each include a sensing gate provided by a receptor material disposed on a dielectric layer overlying a FET channel region disposed at a reaction site, and a control gate provided by a gate electrode (e.g., polysilicon) disposed on a dielectric layer overlying the FET channel region.

Addressable array 300 shows an array formation designed to detect small signal changes provided by biomolecules or bio-entities introduced to bioFET sensors 304. The arrayed format using bit lines 306 and word lines 308 allows for a smaller number of input/output pads since common terminals of different FETs in the same row or column are tied together. Amplifiers may be used to enhance the signal strength to improve the detection ability of the device having the circuit arrangement of schematic 300. In some embodiments, when voltage is applied to particular word lines 308 and bit lines 306, the corresponding access transistors 302 will be turned ON (e.g., like a switch). When the gate of the associated bioFET sensor 304 (e.g., such as back-side gate 222 of the dual gate back-side sensing FET sensor 200) has its charge affected by the bio-molecule presence, a threshold voltage of bioFET sensor 304 is changed, thereby modulating the current (e.g., $I_{ds}$) for a given voltage applied to back-side gate 222. The change of the current (e.g., $I_{ds}$) or threshold voltage ($V_t$) can serve to indicate detection of the relevant biomolecules or bio-entities.

Figure 4:
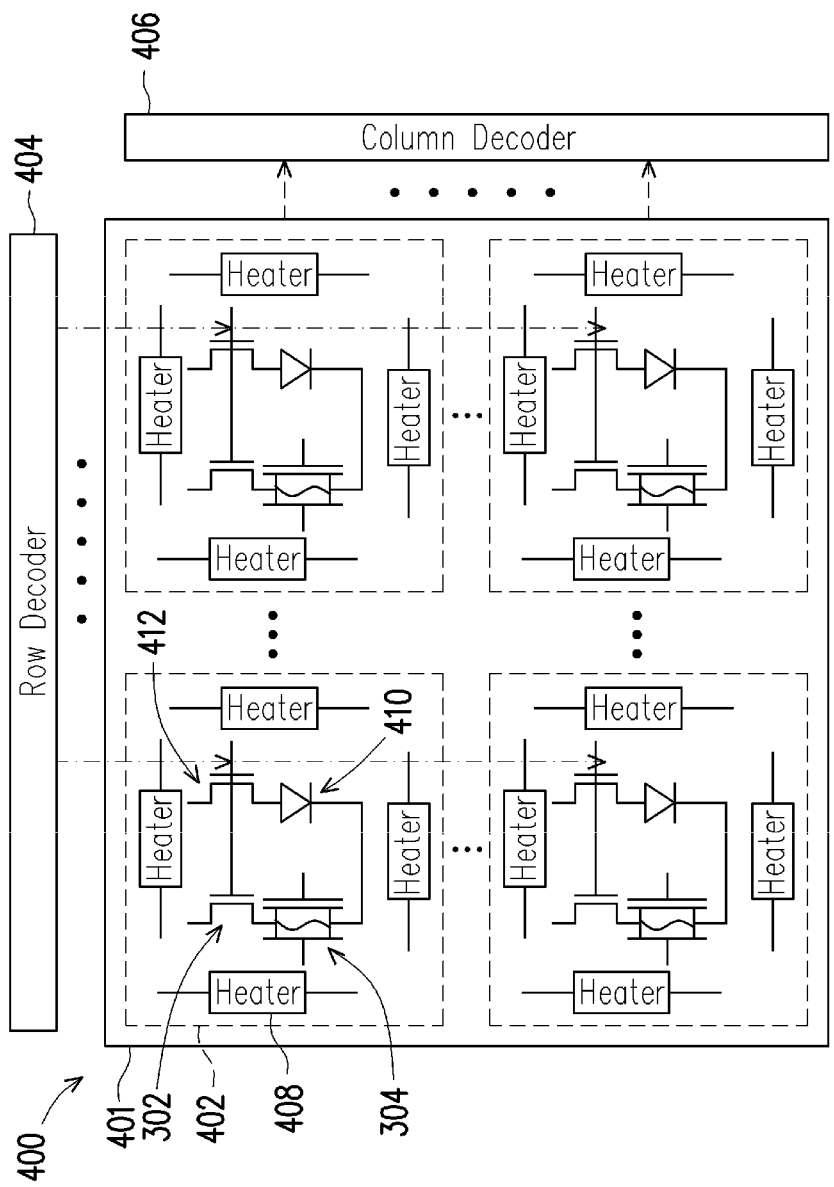
FIG. 4 is a circuit diagram of an exemplary addressable array of dual gate FET sensors and heaters, according to some embodiments.

Referring to FIG. 4, an exemplary schematic 400 is presented. Exemplary schematic 400 includes access transistor 302 and bioFET sensor 304 arranged as an array 401 of individually addressable pixels 402. Array 401 may include any number of pixels 402. For example, array 401 may include 128×128 pixels. Other arrangements may include 256×256 pixels or non-square arrays such as 128×256 pixels.

Each pixel 402 includes access transistor 302 and bioFET sensor 304 along with other components that may include one or more heaters 408 and a temperature sensor 410. In this example, access transistor 302 is an n-channel FET. An n-channel FET 412 may also act as an access transistor for temperature sensor 410. In some embodiments, the gates of FETs 302 and 412 are connected, though this is not required. Each pixel 402 (and its associated components) may be individually addressed using row decoder 404 and column decoder 406. In some embodiments, each pixel 402 has a size of about 10 micrometers by about 10 micrometers. In some embodiments, each pixel 402 has a size of about 5 micrometers by about 5 micrometers or has a size of about 2 micrometers by about 2 micrometers.

Column decoder 406 and row decoder 404 may be used to control the ON/OFF state of both n-channel FETs 302 and 412 (e.g., voltage is applied to the gates of FETs 302 and 412 together, and voltage is applied to the drain regions of FETs 302 and 412 together). Turning ON n-channel FET 302 provides a voltage to an S/D region of bioFET sensor 304. When bioFET sensor 304 is ON, a current $I_{ds}$ flows through bioFET sensor 304 and may be measured.

Heater 408 may be used to locally increase a temperature around bioFET sensor 304. Heater 408 may be constructed using any known technique, such as forming a metal pattern with a high current running through it. Heater 408 may also be a thermoelectric heater/cooler, like a Peltier device. Heater 408 may be used during certain biological tests such as to denature DNA or RNA or to provide a binding environment for certain biomolecules. Temperature sensor 410 may be used to measure the local temperature around bioFET sensor 304. In some embodiments, a control loop may be created to control the temperature using heater 408 and the feedback received from temperature sensor 410. In some embodiments, heater 408 may be a thermoelectric heater/cooler that allows for local active cooling of the components within pixel 402.

Figure 5A:
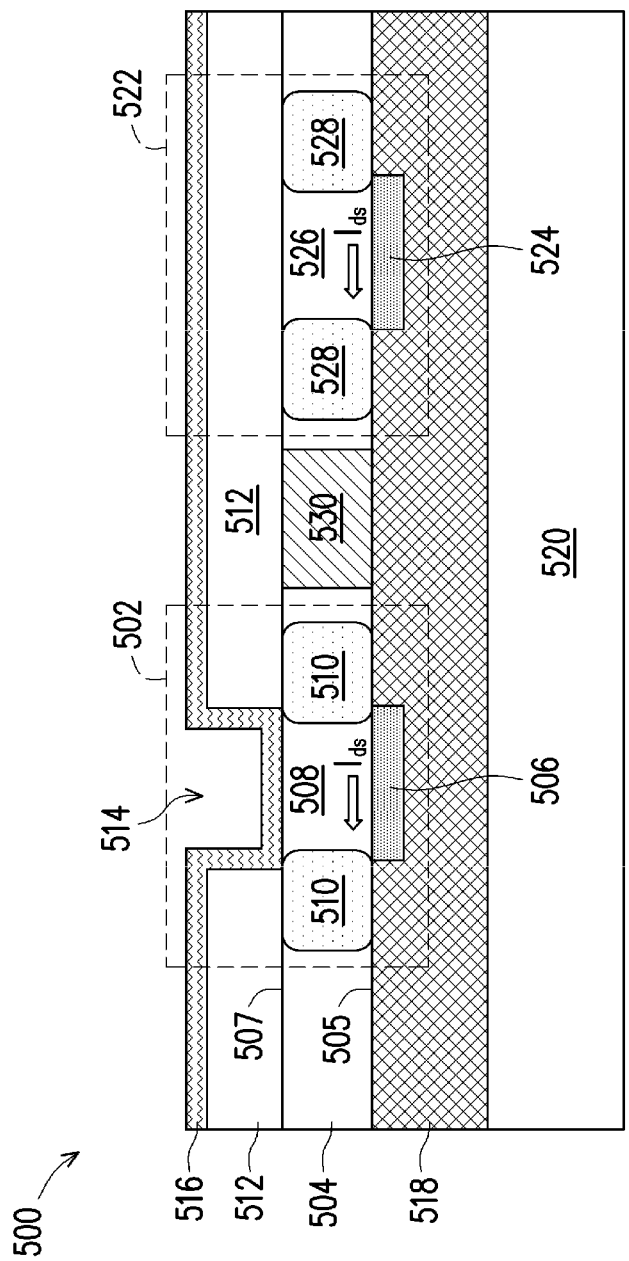
FIGS. 5A and 5B illustrate a cross-sectional view of an exemplary dual gate back-side sensing FET sensor and a non-sensing FET, according to some embodiments.

Referring to FIG. 5A, a cross section of a semiconductor device 500 having a dual gate back-side sensing FET sensor 502 and an access transistor 522 is provided, according to some embodiments. Dual gate back-side sensing FET sensor 502 includes gate 506, S/D regions 510 on either side of gate 506, and a channel region 508 between S/D regions 510 formed within a substrate 504. A gate dielectric layer also exists between gate 506 and channel region 508, but is not shown in the figure. For convenience in describing certain elements, substrate 504 is illustrated as having a front surface 505 and an opposite, parallel back surface 507. It should be noted that the various components of FIG. 5A are not intended to be drawn to scale and are exaggerated for visual convenience, as would be understood by a person skilled in the relevant art.

Dual gate back-side sensing FET sensor 502 includes an interface layer 516 deposited over an isolation layer 512 and within an opening 514 over channel region 508. In some embodiments, interface layer 516 has a thickness between about 20 Å and about 40 Å. Interface layer 516 may be a high-K dielectric material such as, for example, hafnium silicate, hafnium oxide, zirconium oxide, aluminum oxide, tantalum pentoxide, hafnium dioxide-alumina ($HfO_2$—$Al_2O_3$) alloy, or any combinations thereof. Interface layer 516 may act as a support for the attachment of capture reagents as will be discussed in more detail below in the section directed to biological sensing. A solution containing capture reagents, target reagents, wash solution, or any other biological or chemical species may be provided within opening 514 over channel region 508. Further details regarding the fabrication process of dual gate back-side sensing FET sensor 502 may be found in co-owned U.S. Pat. No. 9,080,969, the disclosure of which is incorporated by reference herein.

Access transistor 522 may be coupled to dual gate back-side sensing FET sensor 502 in an arrangement such as that illustrated in FIG. 3 with access transistor 302 and FET sensor 304, according to some embodiments. Access transistor 522 similarly includes a gate 524, S/D regions 528 on either side of gate 524, and a channel region 526 between S/D regions 528 formed within substrate 504. Access transistor 522 includes isolation layer 512 over its channel region 526 (i.e., no opening is formed through isolation layer 512 over channel region 526.) As shown in FIG. 5, interface layer 516 may still be deposited on isolation layer 512 over access transistor 522. Access transistor 522 may be separated from dual gate back-side sensing FET sensor 502 using shallow trench isolation (STI) 530 as would be understood by a person skilled in the relevant art.

In some embodiments, gate 506, gate 524, S/D regions 510, and S/D regions 528 are coupled to various layers of metal interconnects within interconnect region 518. The metal interconnects may be used to make electrical connection with various doped regions and other devices formed within substrate 504. Any number of levels of metal interconnects, along with metal plugs connecting between levels, may be used in interconnect region 518. The process of forming such metal interconnects would be understood by a person skilled in the relevant art.

Semiconductor device 500 may also include a carrier substrate 520 coupled to interconnect region 518, according to some embodiments. Carrier substrate 520 may include one or more conductive portions to make electrical connection with certain metal interconnects of interconnect region 518. Carrier substrate 520 may be used to provide physical support and stability to the thin layers that make up substrate 504 and interconnect region 518.

Dual gate back-side FET sensor 502 may be coupled to additional circuitry fabricated within substrate 504. The additional circuitry may include MOSFET devices, resistors, capacitors, and/or inductors to form circuitry to aid in the operation of dual gate back-side sensing FET sensor 502. The circuitry may represent a readout circuit used to measure a signal from dual gate back-side FET sensor 502 that is indicative of analyte detection. The circuitry may include amplifiers, analog to digital converters (ADCs), digital to analog converters (DACs), voltage generators, logic circuitry, and/or DRAM memory, to name a few examples. All or some of the components of the additional circuitry may be integrated in substrate 504. It should be understood that many bioFET sensors, each substantially similar to dual gate back-side FET sensor 502, may be integrated in substrate 504 and coupled to the additional circuitry. In another example, all or some of the components of the additional circuitry are provided on another semiconductor substrate separate from substrate 504. In yet another example, some components of the additional circuitry are integrated in substrate 504, and some components of the additional circuitry are provided on another semiconductor substrate.

Figure 5B:
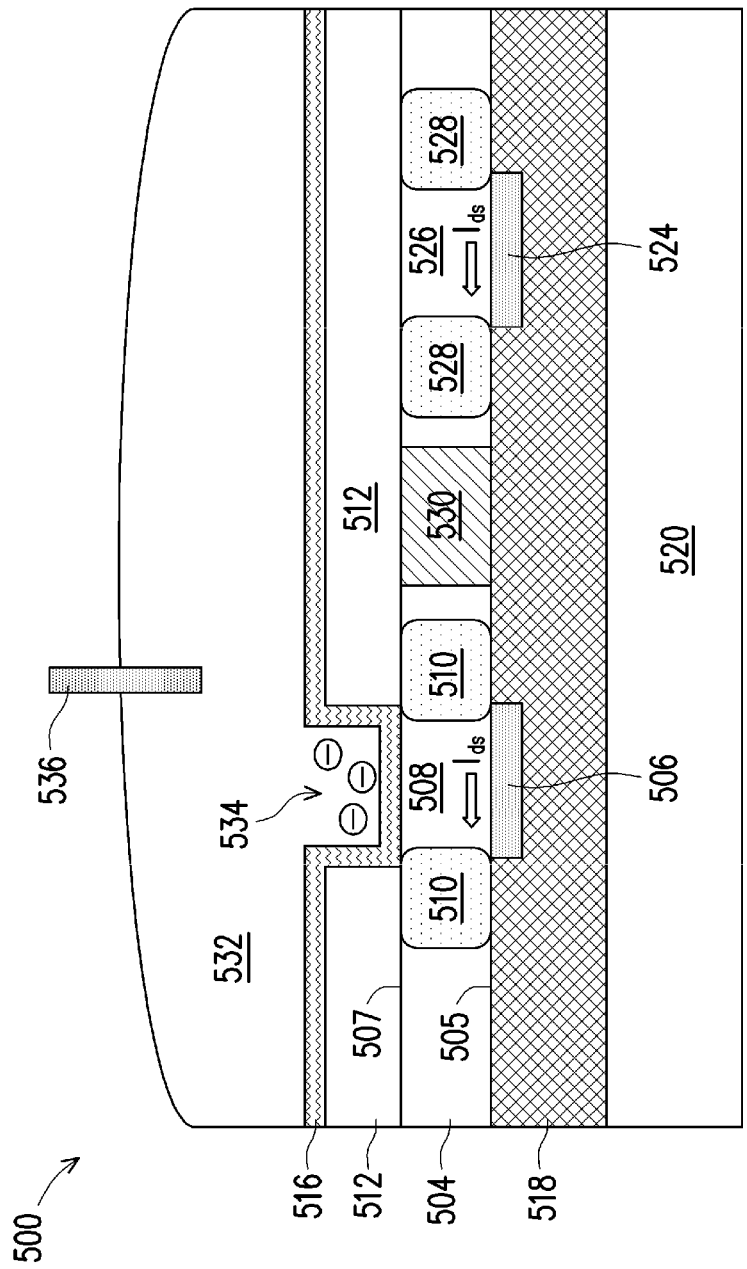

FIG. 5B illustrates a semiconductor device 500 with a fluid 532 disposed over the FETs. Fluid 532 may include an ion concentration 534 that is generated due to, for example, a change in pH of fluid 532, enzymatic reactions between target analytes and capture reagents, binding reactions between target analytes and capture reagents, or other biological interactions. A fluid gate 536 may be provided to form the backside gate of dual gate back-side FET sensor 502. The presence of ion concentration 534 near channel region 508 affects the operation of backside gate of dual gate back-side FET sensor 502 and can be detected as a change in the drain current $I_{ds}$ for a given potential applied to either gate 506 or fluid gate 536. Some example detection studies using dual gate back-side FET sensor 502 are discussed in more detail below.

Fluid 532 may be provided into opening 514 by flowing through a microfluidic channel disposed over back surface 507, according to some embodiments. The microfluidic channel may be bonded directly to either interface layer 516 or isolation layer 512. The microfluidic channel may be molded from a polymer material such as polydimethylsiloxane (PDMS) or polyethylene glycol (PEG). In some embodiments, fluid 532 is disposed in a microfluidic well that quiescently holds fluid 532 and allows fluid 532 to enter through opening 514.

Figure 6A:
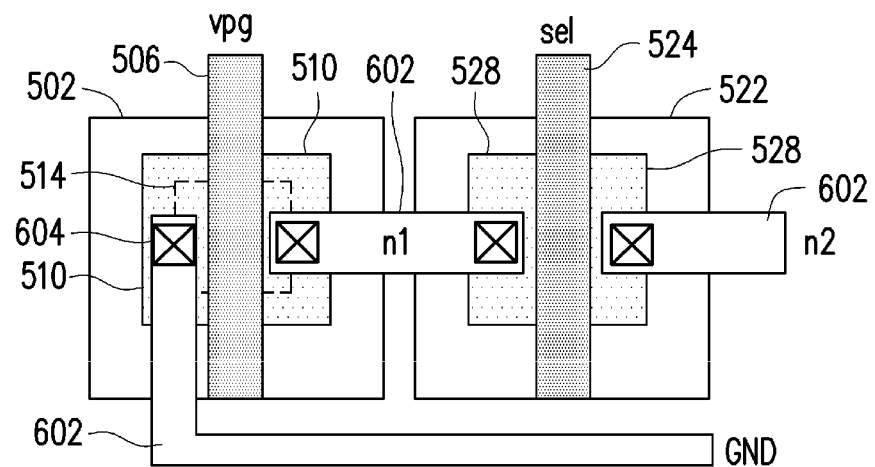
FIG. 6A illustrates a layout of a dual gate back-side sensing FET sensor and a non-sensing FET, according to some embodiments.

FIG. 6A illustrates an example layout of dual gate back-side FET sensor 502 and access transistor 522, according to some embodiments. Similar elements to those illustrated in FIG. 5 are identified with the same labels in FIG. 6A. Opening 514 is illustrated as being slightly wider than gate 506 in order to be seen in the top-down view. The exact size of opening 514 may vary within the bounds of S/D regions 510. However, in this device, opening 514 only exposes the channel region (aligned with gate 506) of a single dual gate back-side FET sensor 502. Metal layers 602 are used to make electrical contact through contacts 604 to S/D regions 510 of dual gate back-side FET sensor 502 and S/D regions 528 of access transistor 522. Metal layers 602 and contacts 604 may be provided within interconnect region 518 in FIG. 5.

Figure 6B:
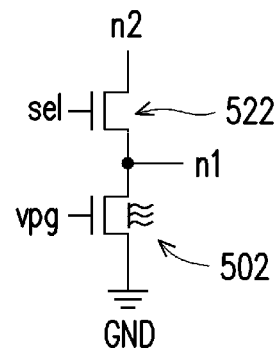
FIG. 6B illustrates a circuit representation of the layout of a dual gate back-side sensing FET sensor and a non-sensing FET, according to some embodiments.

FIG. 6B illustrates an example circuit representation of dual gate back-side FET sensor 502 and access transistor 522 that corresponds with the layout illustrated in FIG. 6A, according to some embodiments. A voltage (vpg) may be applied to gate 506 of dual gate back-side FET sensor 502 to bias the sensor (e.g., to an ON state) during a sensing operation. To measure a current from dual gate back-side FET sensor 502, a voltage (sel) may be applied to gate 524 of access transistor 522. If voltage is also applied to terminal n2, then a current may flow through both dual gate back-side FET sensor 502 and access transistor 522. A magnitude of the current may be affected by any target analytes detected by dual gate back-side FET sensor 502 as will be described in more detail below.

Opening 514 as illustrated in both FIG. 5A and FIG. 6A has a width that is on the order of the gate length of dual gate back-side FET sensor 502, according to some embodiments. Opening 514 is typically constrained to only exposing channel region 508 of dual gate back-side FET sensor 502 to avoid having fluid 532 affect the operation of other FETs in substrate 504 (such as access transistor 522.) It can be difficult for fluid 532 to enter opening 514 due to surface tension forces and hydrophobicity of interface layer 516. These factors contribute to preventing fluid 532 from wetting the surface of interface layer 516 directly above channel region 508. Due to the illustrated layout of semiconductor device 500 (with dual gate back-side FET sensor 502 and access transistor 522 substantially side-by-side), extension of opening 514 may also expose channel region 526 of access transistor 522, which affects the operation of access transistor 522.

Figure 7A:
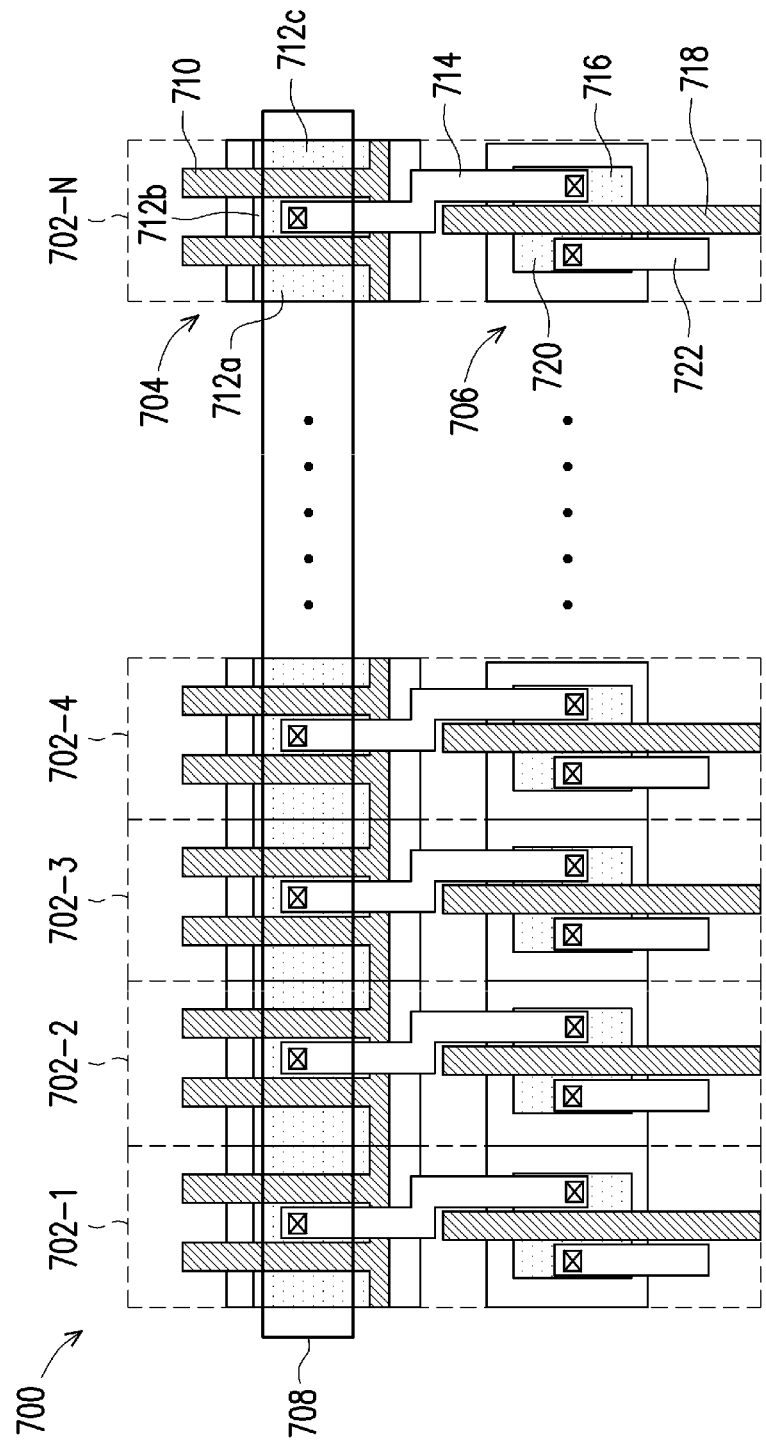
FIG. 7A illustrates a layout of multiple pixels of dual gate back-side sensing FET sensors and non-sensing FETs with a common sensing well, according to some embodiments.

According to some embodiments, a plurality of dual gate back-side FET sensors are arranged side-by-side in a row to allow for an extended opening to span across each of the dual gate back-side FET sensors. FIG. 7A illustrates an example layout 700 of a plurality of pixels 702-1 through 702-N arranged in a single row with each pixel having a dual gate back-side FET sensor 704 and an access transistor 706, according to some embodiments. It should be understood that any following description of a single pixel equally pertains to all other pixels in the array. Furthermore, although only a single row of pixels is illustrated, it should be understood that many rows of pixels may be used to provide a 2-dimensional matrix of pixels, each containing a dual gate back-side FET sensor and a corresponding access transistor. Using a pixel layout such as the one illustrated in FIG. 7A vs. the pixel layout illustrated in FIG. 6A results in about a 20% reduction in the device footprint of the sensor array.

Layout 700 includes an opening 708 to expose the channel regions of each dual gate back-side FET sensor 704, according to some embodiments. Since each of the dual gate back-side FET sensors across the row of pixels are arranged side-by-side, opening 708 may span across the entire row of pixels (e.g., in the X-direction.)

As shown in pixel 702-N, each dual gate back-side FET sensor 704 may have a gate structure 710 that includes two gates over two channel regions with S/D regions 712a, 712b, and 712c arranged between the two gates, according to some embodiments. S/D region 712b may be electrically connected with S/D region 716 of access transistor 706 using metal interconnect 714. This design of dual gate back-side FET sensor 704 with two gates effectively doubles the current output of each dual gate back-side FET sensor 704 by flowing a first current from 712b to 712a and a second current from 712b to 712c when dual gate back-side FET sensor 704 is biased ON. S/D regions 712a and 712c may be grounded. According to an embodiment, each dual gate back-side FET sensor 704 has its S/D regions 712a and 712c. S/D regions 712a and 712c may represent the source terminal of each dual gate back-side FET sensor 704 when each dual gate back-side FET sensor 704 is an n-channel device. S/D regions 712a and 712c may represent the drain terminal of each dual gate back-side FET sensor 704 when each dual gate back-side FET sensor 704 is a p-channel device. Due to the side-by-side layout of each dual gate back-side FET sensor 704, adjacent FET sensors may share the same S/D region 712a and 712c.

It should be understood that using a two-gate design in each pixel as illustrated in FIG. 7A is only one example, and that a single-gate design may be used as well in one or more or all of the pixels. An example of the single-gate design is illustrated in the layout diagram of dual gate back-side FET sensor 502 in FIG. 6A. By sharing S/D regions 712a and 712c across adjacent pixels, the overall size of the sensing array may be reduced by eliminating dead space between adjacent pixels.

According to some embodiments, gate structure 710 of each dual gate back-side FET sensor 704 across pixels 702-1 to 702-N are coupled together. In this way, each dual gate back-side FET sensor 704 may be biased ON at the same time, and choosing which sensor to measure from is performed via an applied voltage to gate 718 of a specific access transistor 706. S/D region 720 of each access transistor 706 may be electrically coupled to a voltage source through metal interconnect 722. According to an embodiment, the S/D regions 720 of each access transistor 706 are electrically coupled together, such that only voltage applied to gate 718 determines which access transistor 706 is biased ON. Furthermore, current from a corresponding dual gate back-side FET sensor 704 may be measured from any node electrically connected to metal interconnect 722.

Figure 7B:
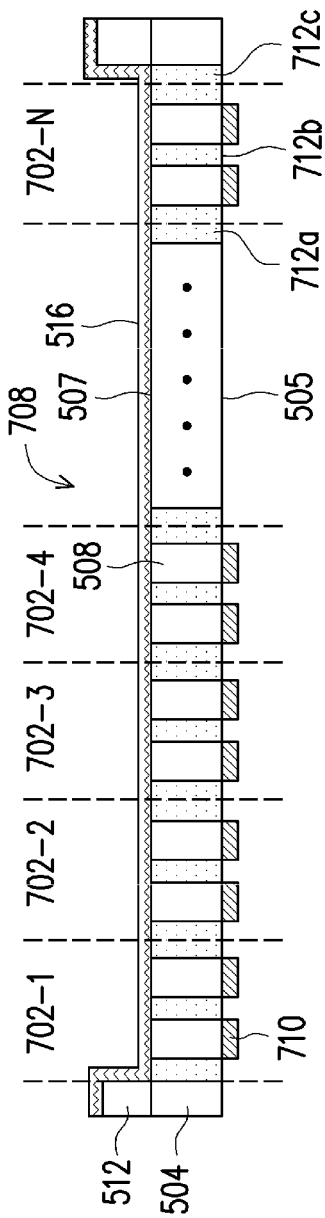
FIG. 7B illustrates a side view of dual gate back-side sensing FET sensors in a row with the common sensing well, according to some embodiments.

FIG. 7B illustrates a cross-section view taken across a row of dual gate back-side FET sensors 704 between pixels 702-1 and 702-N, according to some embodiments. Opening 708 stretches across multiple bioFET sensors in the X-direction to expose a portion of back surface 507 of substrate 504. The exposed portion of back surface 507 includes the surfaces of a plurality of channel regions 508 spanning across more than one dual gate back-side FET sensor. Front surface 505 of substrate 504 includes a plurality of gates 710 patterned over channel regions 508.

Interface layer 516 is disposed within opening 708 to provide a surface for binding various capture reagents, according to some embodiments. Due to the larger width of opening 708, a fluid carrying either the capture reagents or target analytes that interact with the capture reagents have easier access to interface layer 516 directly on back surface 507.

The fluid may be provided into opening 708 by flowing the fluid through a microfluidic channel disposed over back surface 507, according to some embodiments. The microfluidic channel may be bonded directly to either interface layer 516 or isolation layer 512. The microfluidic channel may be molded from a polymer material such as, for example, polydimethylsiloxane (PDMS) or polyethylene glycol (PEG). The microfluidic channel may run along the X direction such that fluid flows in the X-direction across opening 708. In some embodiments, a different microfluidic channel is provided for each row of dual gate back-side FET sensors 704 in a two-dimensional sensing array. In other embodiments, a microfluidic channel includes a width that is wide enough to encompass more than one, or all, rows of dual gate back-side FET sensors 704 in the two-dimensional sensing array.

In some embodiments, the fluid is disposed in a microfluidic well that quiescently holds the fluid and allows the fluid to enter through opening 708. According to some embodiments, the microfluidic well holds between about 1 µL and about 100 µL of fluid. The microfluidic well may be sized and positioned such that only a portion of the total number of dual gate back-side FET sensors 704 in a two-dimensional sensing array are exposed to the fluid within the well. In another example, all of the dual gate back-side FET sensors 704 in a two-dimensional sensing array are exposed to the fluid within the well.

Figure 7C:
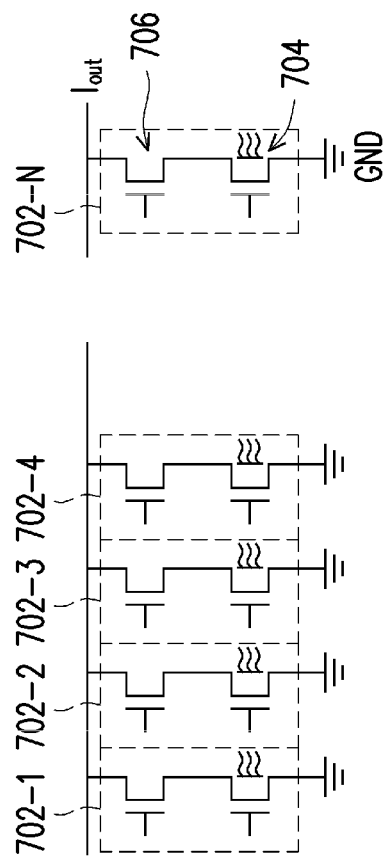
FIG. 7C illustrates a circuit representation of the layout of multiple pixels of dual gate back-side sensing FET sensors and non-sensing FETs, according to some embodiments.

FIG. 7C illustrates a circuit representation of layout 700, according to some embodiments. The row of pixels 702-1 through 702-N are shown with each access transistor 706 having its drain terminal (in the case of an n-channel device) connected together for measuring a current $I_{out}$, from the selected dual gate back-side FET sensor 704.

Opening 708 may stretch across the entire extent of a given row of pixels 702-1 to 702-N, or may stretch across a subset of the pixels 702-1 to 702-N. The total number of pixels (N) in a row may be as few as 2 and as many as 4096. Additionally, opening 708 is not limited to only stretching across one row of pixels. In some embodiments, opening 708 also extends in the Y-direction to expose the channel regions of dual gate back-side FET sensors in other rows. When providing an opening that extends in both X and Y directions to expose the channel regions of multiple dual gate back-side FET sensors in a two-dimensional array, each of the access transistors 706 may be located outside of the two-dimensional array of dual gate back-side FET sensors.

Figure 8A:
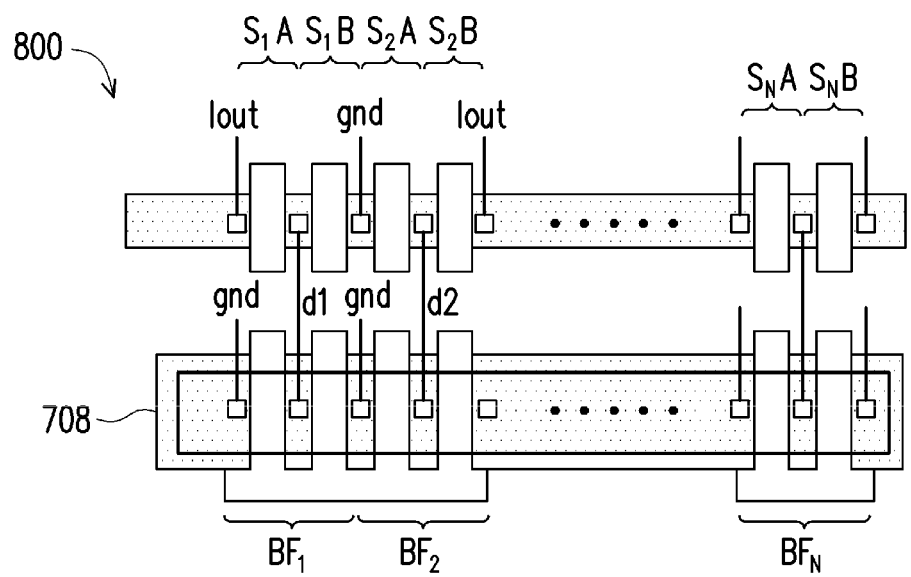
FIG. 8A illustrates a layout of multiple dual gate back-side sensing FET sensors and non-sensing FETs with a common sensing well, according to some embodiments.

FIG. 8A illustrates another layout 800 of dual gate back-side FET sensors $BF_1$-$BF_N$, according to some embodiments. In layout 800, dual gate back-side FET sensors $BF_1$-$BF_N$ are again arranged in a same row side-by-side such that an opening 708 spans across multiple sensors to expose channel regions of each dual gate back-side FET sensor $BF_1$-$BF_N$. However, unlike layout 700, each dual gate back-side FET sensor is electrically coupled with two other FET devices. In the illustrated example, dual gate back-side FET sensor $BF_1$ is coupled with access transistor $S_1A$ and shunt transistor $S_1B$ while dual gate back-side FET sensor $BF_2$ is coupled with access transistor $S_2A$ and shunt transistor $S_2B$. This same arrangement may be repeated for each pixel in the row.

It should be understood that using a two-gate design for each dual gate back-side FET sensor $BF_1$-$BF_N$ as illustrated in FIG. 8A is only one example, and that a single-gate design may be used as well. An example of the single-gate design is illustrated in the layout diagram of dual gate back-side FET sensor 502 in FIG. 6A. Also by sharing grounded S/D regions between adjacent sensors, the overall size of the sensing array may be reduced by eliminating dead space between adjacent sensors.

Figure 8B:
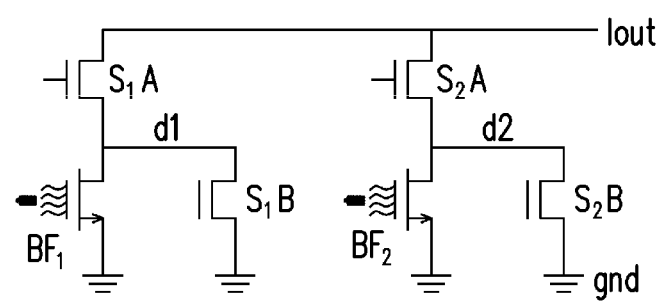
FIG. 8B illustrates a circuit representation of the layout of dual gate back-side sensing FET sensors and non-sensing FETs, according to some embodiments.

FIG. 8B illustrates a circuit representation of layout 800 with the same labels used from FIG. 8A to identify the same elements, according to some embodiments. An example operation will now be provided to describe the function of the shunt transistor. When a current is desired to be measured from dual gate back-side FET sensor $BF_1$, a voltage is applied to the gate of access transistor $S_1A$ to bias the transistor ON, thus creating a conductive path to $BF_1$, and current Iout can be measured. When access transistor $S_1A$ is biased ON, shunt transistor $S_1B$ is biased to be off to cut off the shunted path to ground. According to an embodiment, an inverter is used to ensure that the signal received at the gate of access transistor $S_1A$ is inverted compared to the signal received at the gate of shunt transistor $S_1B$. The inverter may be arranged in each pixel to ensure correct operation of each access transistor $S_1A$ and shunt transistor $S_1B$. The inventor may also be coupled with a NAND gate having inputs from corresponding bit and word lines for the given pixel.

Because current from only dual gate back-side FET sensor $BF_1$ is desired, access transistor $S_2A$ is biased to be off. Shunt transistor $S_2B$ is biased to be ON to ensure that no voltage is applied to the unselected dual gate back-side FET sensor $BF_2$. If shunt transistor $S_2B$ were not used, a floating (e.g., unknown) voltage potential may exist and cause unwanted current flow through $BF_2$. The same description applies visa-versa when current is desired to be measured from $BF_2$.

Figure 9:
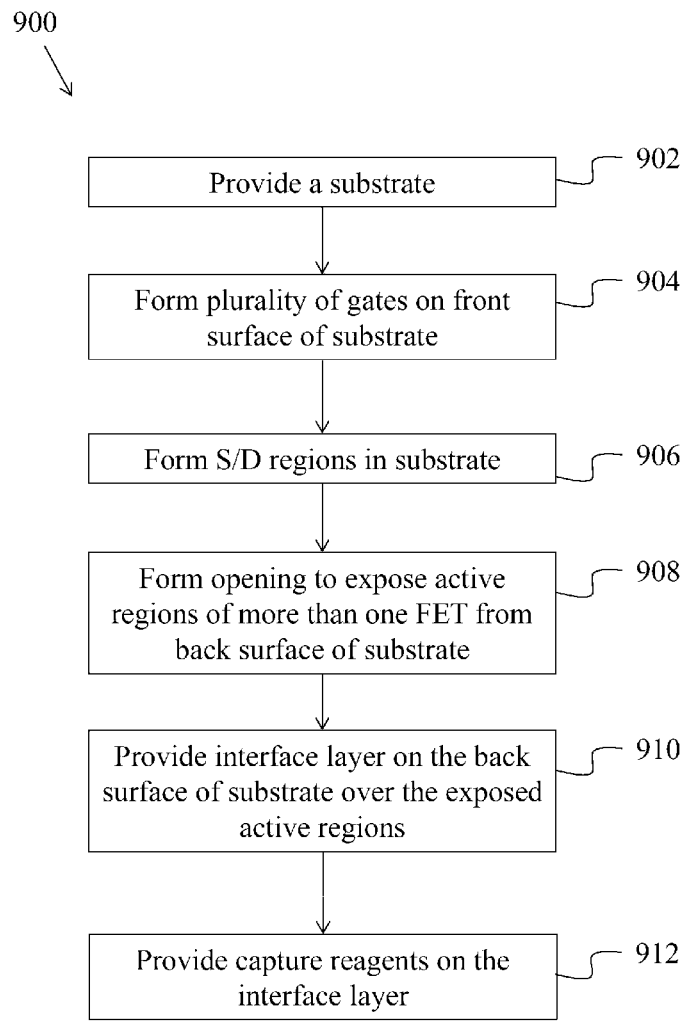
FIG. 9 illustrates a flow diagram of an exemplary method of fabricating a plurality of dual gate back-side sensing FET sensors, according to some embodiments.

FIG. 9 illustrates an example method 900 for fabricating a plurality of dual gate back-side FET sensors such as those illustrated in layouts 700 and 800, according to some embodiments. Method 900 may include forming the dual gate back-side FET sensors using one or more process steps compatible with or typical to a complementary metal-oxide-semiconductor (CMOS) process. It is understood that additional operations can be provided before, during, and after method 900, and some of the steps described below can be replaced or eliminated, for additional embodiments of the method. Further, it is understood that method 900 includes operations having features of a typical CMOS technology process flow and thus, are only described briefly herein. Typical CMOS technology processes may include photolithography; ion implantation; diffusion; deposition including physical vapor deposition (PVD), metal evaporation or sputtering, chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), atomic layer CVD (ALCVD), spin on coating; and etching including wet etching, dry etching, and plasma etching. Reference may be made to certain elements illustrated in FIGS. 5A and 7B.

Method 900 begins at block 902 where a substrate is provided. The substrate may be a semiconductor substrate. The semiconductor substrate may be a silicon substrate. Alternatively, the substrate may include another elementary semiconductor, such as germanium; a compound semiconductor including silicon carbide; an alloy semiconductor including silicon germanium; or combinations thereof. In some embodiments, the substrate is a semiconductor on insulator (SOI) substrate. The substrate may include doped regions, such as p-wells and n-wells. In the present disclosure, a wafer is a workpiece that includes a semiconductor substrate and various features formed in and over and attached to the semiconductor substrate. The wafer may be in various stages of fabrication and is processed using the CMOS process. After the various stages of fabrication are completed, the wafer is separated into individual dies that are packaged into an integrated chip.

Method 900 then proceeds to block 904 where a plurality of gates are formed on a front surface of the substrate. A first set of the plurality of gates may act as gates of dual gate back-side FET sensors while a second set of the plurality of gates may act as gates of various other transistors in the substrate, such as access transistors and/or shunt transistors. According to some embodiments, the gates are polysilicon. Other exemplary gate materials include metals such as, copper (Cu), tungsten (W), titanium (Ti), tantalum (Ta), chromium (Cr), platinum (Pt), silver (Ag), gold (Au); suitable metallic compounds like titanium nitride (TiN), tantalum nitride (TaN), nickel silicide (NiSi), cobalt silicide (CoSi); combinations thereof; and/or other suitable conductive materials.

A gate dielectric is provided between the plurality of gates and the front surface of the substrate. In some embodiments, the gate dielectric is silicon oxide. Other exemplary gate dielectrics include silicon nitride, silicon oxynitride, a dielectric with a high dielectric constant (high k), or combinations thereof. Examples of high k materials include hafnium silicate, hafnium oxide, zirconium oxide, aluminum oxide, tantalum pentoxide, hafnium dioxide-alumina ($HfO_2$—$Al_2O_3$) alloy, or combinations thereof.

Method 900 proceeds to block 906 where S/D regions are formed in the substrate on either side of each of the plurality of gates. The S/D regions may include n-type dopants or p-type dopants depending on the FET configuration (i.e., n-channel or p-channel.) S/D regions of both the dual gate back-side FET sensors and other transistors, such as access transistors and/or shunt transistors, may be formed at the same time. Additional interconnect layers may be formed to create electrical connections to each of the plurality of gates and S/D regions, such as those formed within interconnect region 518.

A carrier substrate 520 may also be attached to interconnect region 518 to allow for various subsequent operations to the back side of the substrate without affecting the structural integrity of the semiconductor substrate. In some embodiments, the carrier substrate 520 is bonded to a last metal interconnect layer of interconnect region 518. In some embodiments, carrier substrate 520 is bonded to a passivation layer formed on the interconnect region. The carrier substrate may be attached to the device substrate using fusion, diffusion, eutectic, and/or other suitable bonding methods. Exemplary compositions for the carrier substrate include silicon, glass, and quartz. In some embodiments, the carrier substrate may include other functionality such as interconnect features, bonding sites, defined cavities, and/or other suitable features. The carrier substrate may be removed during subsequent processing (e.g., after thinning).

Method 900 proceeds to block 908 where an opening is formed through a dielectric layer on the back side of the substrate, according to some embodiments. For example, an opening 708 may be etched through isolation layer 512 to expose the back side 507 of substrate 504. According to some embodiments, opening 708 is large enough to expose the channel regions 508 of more than one dual gate back-side FET sensor. Opening 708 may span across a row of dual gate back-side FET sensors arranged side-by-side.

The opening may be formed by first performing a dry etch such as a reactive ion etch (RIE) or any plasma etch to thin the dielectric layer on the back side of the substrate. Afterwards, the thin remaining portion of the dielectric layer within the opening may be removed using a wet etch, such as a buffered oxide etch (BOE) or hydrofluoric acid (HF).

Method 900 proceeds to block 910 where an interface layer 516 is disposed on the back surface of the substrate over the exposed channel regions within the opening, according to some embodiments. The interface layer is compatible for biomolecule or bio-entity binding. For example, the interface layer may provide a binding interface for biomolecules or bio-entities. The interface layer may include a dielectric material, a conductive material, and/or other suitable material for holding a receptor. Exemplary interface materials include high-k dielectric films, metals, metal oxides, dielectrics, and/or other suitable materials. As a further example, exemplary interface layer materials include: hafnium oxide ($HfO_2$), tantalum oxide ($Ta_2Os$), Pt, Au, W, Ti, aluminum (Al), Cu; oxides of such metals such as, for example, silicon dioxide ($SiO_2$), silicon nitride ($Si_3N_4$), aluminum oxide ($Al_2O_3$), titanium oxide ($TiO_2$), TiN, zirconium oxide ($ZrO_2$), tin (II) oxide (SnO), tin dioxide ($SnO_2$); and/or other suitable materials. The interface layer may be formed using CMOS processes such as, for example, physical vapor deposition (PVD) (sputtering), chemical vapor deposition (CVD), plasma-enhanced chemical vapor deposition (PECVD), atmospheric pressure chemical vapor deposition (APCVD), low-pressure CVD (LPCVD), high density plasma CVD (HDPCVD), or atomic layer CVD (ALCVD). In some embodiments, the interface layer includes a plurality of layers.

Method 900 continues with block 912 where capture reagents are provided on the interface layer, according to some embodiments. A film treatment or a capture reagent such as an enzyme, antibody, ligand, peptide, nucleotide, cell of an organ, organism, or piece of tissue may be provided or bound on the interface layer for detection of a target analyte. For instance, to detect single-stranded deoxyribonucleic acid (ssDNA), the interface layer may be functionalized with immobilized complementary ssDNA strands. Also, to detect various proteins such as tumor markers, the interface layer may be functionalized with monoclonal antibodies. The capture reagents may be a part of self-assembled monolayer (SAM) of molecules. The SAM may have head groups of silane groups, silyl groups, silanol groups, phosphonate groups, amine groups, thiol groups, alkyl groups, alkene groups, alkyne groups, azido groups, or expoxy groups. The capture reagents are attached to the head groups of the SAM.

In some embodiments, the same capture reagents are immobilized over all dual gate back-side FET sensors within a given opening. In this example, each of the dual gate back-side FET sensors in the opening may be biased ON when detecting a target analyte, such that the combined current from each dual gate back-side FET sensor is collected. Integrating the combined signal from multiple dual gate back-side FET sensors may help to improve either or both the signal-to-noise ratio and sensitivity of the sensor array with respect to the target analyte. In some embodiments, each row of dual gate back-side FET sensors in a two-dimensional array includes the same capture reagents immobilized over the bioFET sensors of a given row, but may include different capture reagents between different rows.

In some embodiments, different capture reagents are immobilized over different dual gate back-side FET sensors within a given opening. In this example, various target analytes can be detected using the same sensing array. The current measured from a particular dual gate back-side FET sensor would be associated with a concentration of a particular target analyte binding to the corresponding capture reagents immobilized over the particular dual gate back-side FET sensor. Different capture reagents may be disposed over different dual gate back-side FET sensors in the same opening using a liquid dispensing apparatus designed to carefully dispense very small amounts of liquid (e.g., less than 1 nL) in order to immobilize the capture reagents only over a single, or a small number of, dual gate back-side FET sensors.

Piezoelectric Mixer

As discussed above with reference to FIG. 5B, fluid may be introduced over various bioFET sensors arranged in a sensor array via one or more microfluidic channels. Using microfluidic channels to direct fluid flow also provides the ability to integrate other fluidic devices such as pumps and mixers. Mixers can be especially important for enhancing the interactions and reactions occurring between analytes in the fluid and capture molecules on the bioFET sensors.

An integrated mixer provides mechanical force to introduce turbulence into the fluid. The turbulence provides a higher mixing efficiency than diffusion or convection alone. The mixing action works to reduce the incubation time for bio-reactions to occur, such as any binding reactions between analytes in the fluid and capture molecules on the bioFET sensors.

Figure 10:
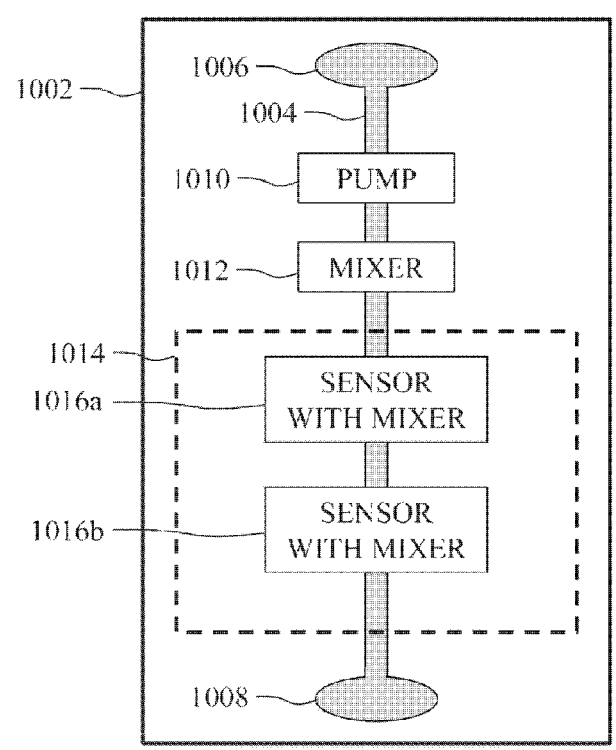
FIG. 10 illustrates an example layout of a biosensing chip, according to some embodiments.

Mixers may be integrated anywhere along the microfluidic channel on the chip. In some embodiments, more than one mixer may be included. FIG. 10 illustrates an example layout of a sensor chip 1002 that includes a microfluidic channel 1004 having an inlet 1006 and an outlet 1008. Microfluidic channel 1004 may be patterned by molding the channel into a polymer material such as polydimethysiloxane (PDMS), or by patterning walls that define the channel on a surface of sensor chip 1002. Microfluidic channel 1004 may have a width of less than 5 mm, less than 3 mm, less than 1 mm, less than 500 µm, less than 300 µm, less than 100 µm, or less than 50 µm.

Each of inlet 1006 and outlet 1008 may be formed by chemical etching, laser drilling, or mechanical drilling through a material that seals the top of microfluidic channel 1004. The material may be a polymer such as PDMS or polyethylene glycol, or the material may be a more rigid substrate such as silicon or silicon dioxide (examples of silicon dioxide include glass, quartz, fused silica, etc.)

According to an embodiment, microfluidic channel 1004 includes an integrated pump 1010. Pump 1010 may be any type of well-known fluidic pump, such as a peristaltic pump, a piezoelectric pump, or an electro-osmotic pump.

According to an embodiment, microfluidic channel 1004 includes an integrated mixer 1012. Mixer 1012 may be a piezoelectric mixer as will be discussed in more detail herein. Mixer 1012 may be integrated in microfluidic channel 1004 upstream of a sensing area 1014 where the bioFET sensor array(s) are located. As such, mixer 1012 may be provided to premix the fluid before it reaches any of the bioFET sensors.

According to an embodiment, microfluidic channel 1004 is designed to deliver fluid to sensing area 1014 having at least a first sensor 1016a and a second sensor 1016b. In one embodiment, each of first sensor 1016a and second sensor 1016b includes its own integrated mixer disposed near or directly over the bioFET sensing surface. This allows for mixing to occur directly at the site where the bio-reactions occur, such as any binding reactions between analytes in the fluid and capture molecules on the bioFET sensors. The integrated mixers over each of sensor 1016a and sensor 1016b may be piezoelectric mixers.

It should be understood that sensor 1016a may represent any number of bioFET sensors, including any number of bioFET sensors arranged in a sensing array. Thus, in an embodiment, sensor 1016a is a first sensor array having its own integrated mixer over the first sensing array, and sensor 1016b is a second sensor array having its own integrated mixer over the second sensing array. In another embodiment, sensor 1016a represents a first group of bioFET sensors having a first common sensing well exposing the backside of each of the bioFET sensors in the first group, and sensor 1016b represents a second group of bioFET sensors having a second common sensing well exposing the backside of each of the bioFET sensors in the second group. The bioFET sensors of the first group and the bioFET sensors of the second group may be arranged in the same sensor array, or may be from different sensor arrays.

Figure 11A:
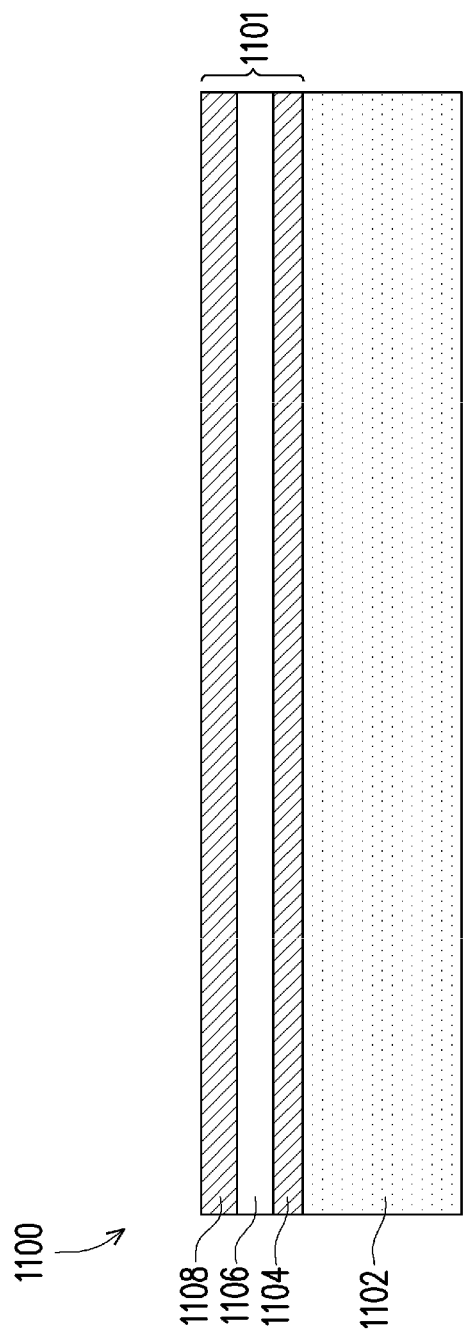
FIGS. 11A-11E illustrate stages of a fabrication process for a piezoelectric mixer, according to some embodiments.

An example fabrication process for a piezoelectric mixer 1100 that may be integrated within microfluidic channel 1004 is illustrated in FIGS. 11A-11E, according to an embodiment. FIG. 11A illustrates a first stage in the fabrication of mixer 1100 where a piezoelectric film stack 1101 is formed on a substrate 1102. Piezoelectric film stack 1101 includes a first electrode layer 1104, a piezoelectric film 1106, and a second electrode layer 1108.

Substrate 1102 may be silicon or silicon dioxide (examples of silicon dioxide include glass, quartz, fused silica, etc.) In an embodiment where substrate 1102 is silicon, an insulating layer may first be deposited over substrate 1102 before the formation of first electrode layer 1104. The insulating layer may be silicon dioxide.

First electrode layer 1104 and second electrode layer 1108 can be the same conductive material. Each of first electrode layer 1104 and second electrode layer 1108 may include platinum or gold, to name a few examples. First electrode layer 1104 and second electrode layer 1108 may be deposited through a deposition technique such as, for example, sputtering, evaporation, or chemical vapor deposition (CVD). First electrode layer 1104 and second electrode layer 1108 may each have a thickness between about 50 nm and about 500 nm.

Piezoelectric film 1106 may include any material having a piezoelectric property. A material with a piezoelectric property exhibits a mechanical strain when subjected to an applied electric field. In one example, lead zirconate titanate (PZT) crystals can change a percentage of their static dimension when an external electric field is applied to the material. PZT can be used for micro-scale applications due to its relative ease of depositing into a thin layer, marked demonstration of the piezoelectric effect, and its low cost. Other example materials that exhibit the piezoelectric effect and could be used for piezoelectric film 1106 include polyvinylidene fluoride (PVDF) and lithium niobate. Piezoelectric film 1106 may be deposited using, for example, a physical vapor deposition (PVD) or CVD technique. Piezoelectric film 1106 may have a thickness between about 100 nm and 5000 nm.

Figure 11B:
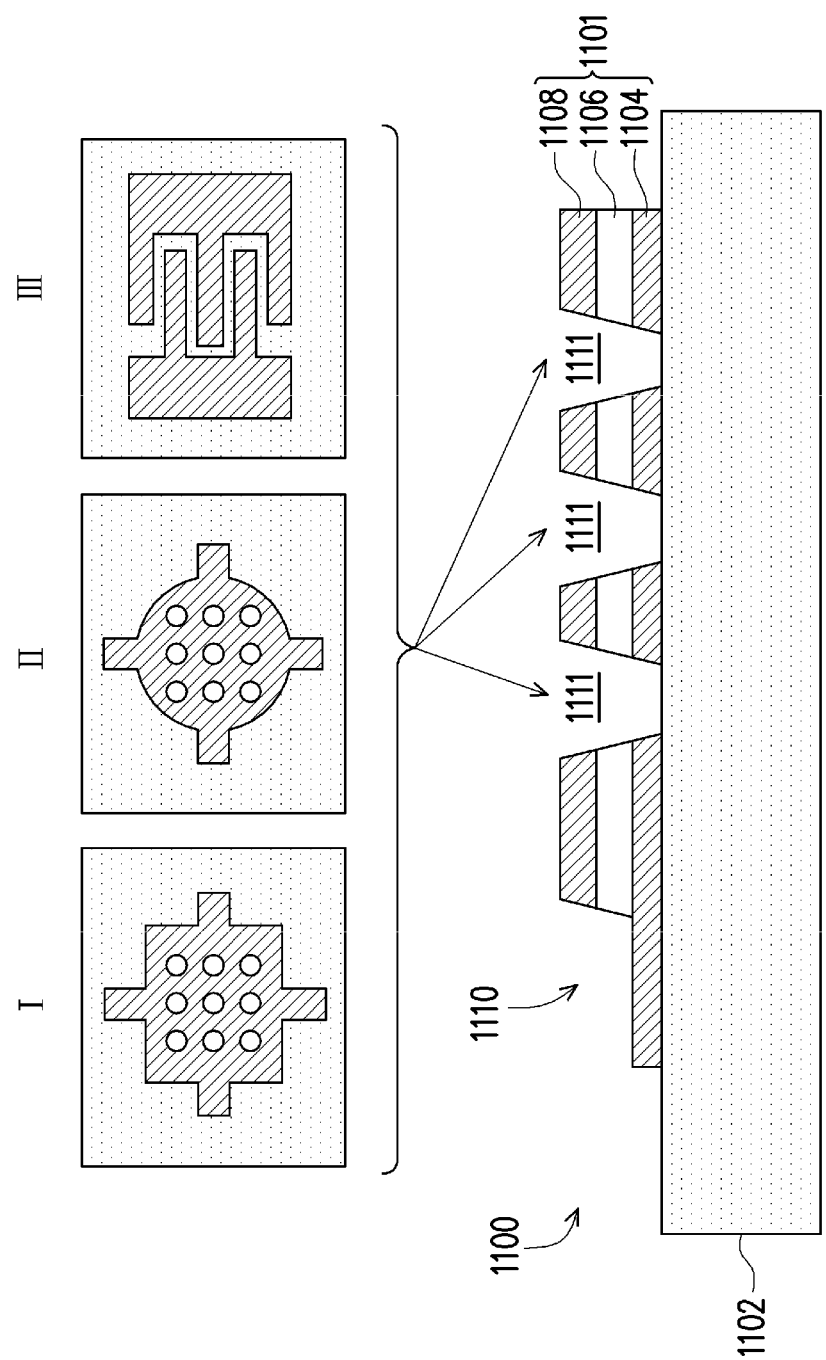

FIG. 11B illustrates a second stage in the fabrication process of mixer 1100, according to an embodiment. A cross-section of mixer 1100 illustrates a plurality of openings 1111 formed by one or more etching processes to etch through a thickness of piezoelectric film stack 1101. Various mask patterns may be used to protect portions of piezoelectric film stack 1101 during the one or more etching processes to form a different mixer pattern when viewed from a top-down perspective. According to some embodiments, piezoelectric film stack 1101 may be etched using ion beam etching with argon. According to some embodiments, piezoelectric film stack 1101 may be etched using hydrochloric acid.

Three example mixer patterns (I, II, and III) are illustrated in FIG. 11B, according to some embodiments. In a first pattern I, a plurality of openings are formed within a generally square portion of piezoelectric film stack 1101. In a second pattern II, a plurality of openings are formed within a generally circular portion of piezoelectric film stack 1101. In a third pattern III, a serpentine opening is formed within a generally square portion of piezoelectric film stack 1101. It should be understood that these patterns are provided merely as examples and are not limiting. The openings themselves may be any shape are not limited to being circular. Similarly, the overall shape of piezoelectric film stack 1101 following the one or more etching processes may be any shape, and are not limited to either circular or square, when viewed from a top-down perspective.

Another etch process may be used to form recess 1110, according to an embodiment. Recess 1110 exposes first electrode layer 1104 after etching through second electrode layer 1108 and piezoelectric film 1106. Electrical connection may be provided more easily to first electrode layer 1104 due to the presence of recess 1110. Electrical connection must be made to each of first electrode layer 1104 and second electrode layer 1108 in order to produce an E-field between first electrode layer 1104 and second electrode layer 1108 that generates mechanical strain in piezoelectric film 1106.

Figure 11C:
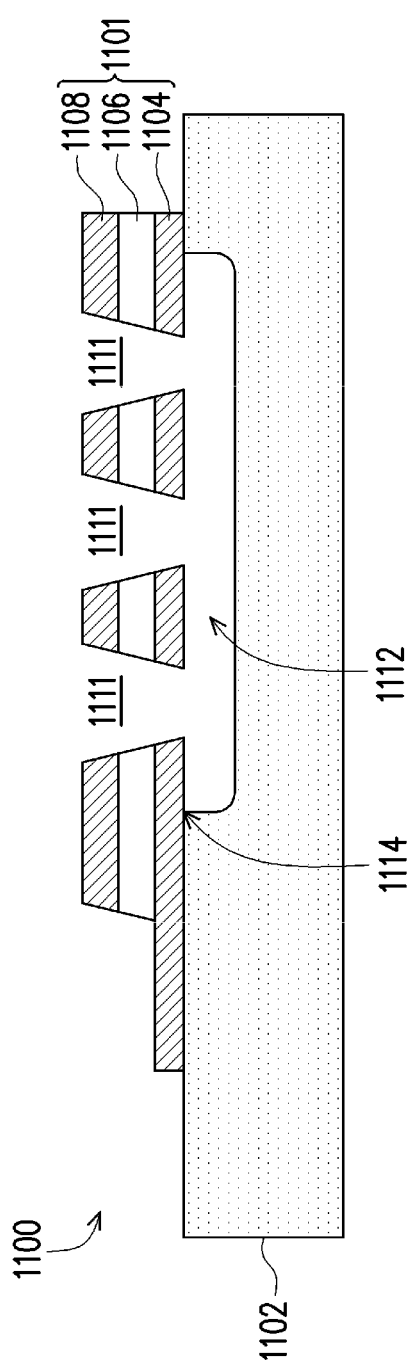

FIG. 11C illustrates a third stage in the fabrication process of mixer 1100, according to an embodiment. An etching process is performed to release a portion of piezoelectric film stack 1101 by removing a portion of substrate 1102 beneath piezoelectric film stack 1101. Substrate 1102 is first protected using a photoresist or hard mask layer everywhere except where piezoelectric film stack 1101 is patterned over substrate 1102. Then, an etching process is performed to etch away a portion of substrate 1102 beneath openings 1111. Since the etch is isotropic, the etching will also continue laterally beneath openings 1111 such that portions of substrate 1102 between openings 1111 are also removed. The result of the etch is illustrated as cavity 1112, according to an embodiment. The "release" etch may be performed using wet etching techniques or dry etching techniques. An example wet etching technique includes exposing substrate 1102 to various possible concentrations of hydrofluoric acid to form cavity 1112 when substrate 1102 is silicon dioxide. Vaporized hydrofluoric acid may also be used to form cavity 1112 when substrate 1102 is silicon dioxide. In an example where substrate 1102 is silicon, a dry etching process using xenon difluoride ($XeF_2$) may be used to form cavity 1112. According to an embodiment, cavity 1112 has a depth between about 100 micrometers and about 250 micrometers.

Figure 11D:
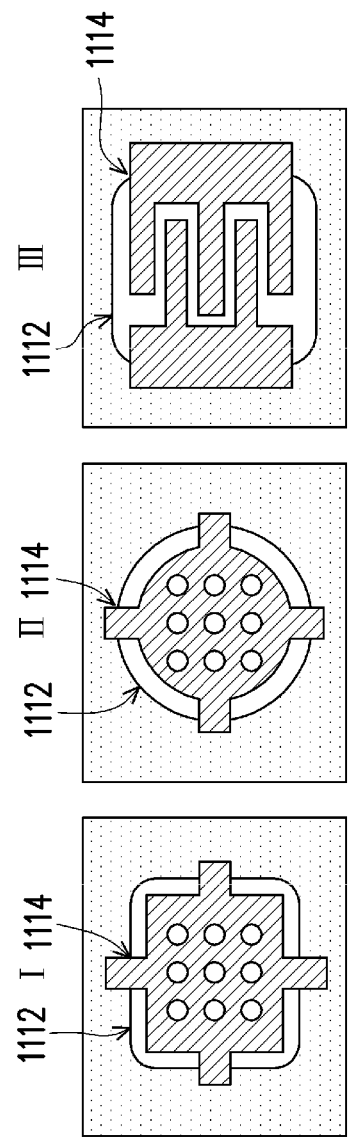

After formation of cavity 1112, mixer 1100 includes a suspended piezoelectric film stack 1101 that is anchored to substrate 1102 via one or more anchor points 1114. FIG. 11D illustrates example top-down views of the same three mixer patterns (I, II, and III) discussed above with reference to FIG. 11B. These example views have been provided again to illustrate cavity 1112 from the top-down perspective, as well as the example locations of anchor points 1114 for each mixer pattern.

Figure 11E:
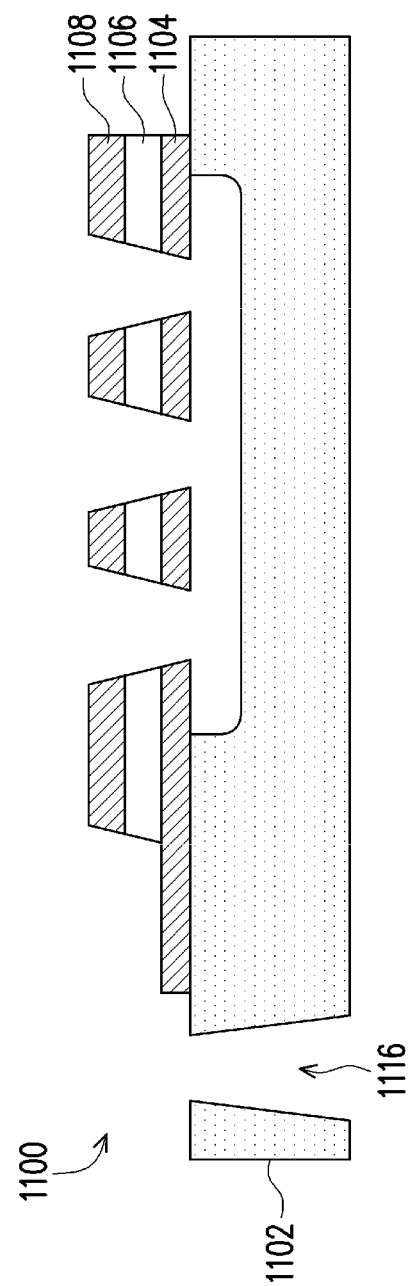

FIG. 11E illustrates a fourth stage in the fabrication process of mixer 1100, according to an embodiment. An opening 1116 is formed through a thickness of substrate 1102 to provide either a fluidic port or an electrical port. The electrical port may be used to make electrical connection with either first electrode layer 1104 or second electrode layer 1108. Opening 1116 may be formed using laser drilling or using wet etchants. For example, potassium hydroxide (KOH) may be used to etch through silicon while hydrofluoric acid may be used to etch through silicon dioxide. Dry etching processes such as deep reactive ion etching (DRIE) may be used as well.

Although a single opening 1116 is illustrated, it should be understood that a plurality of openings may be etched through a thickness of substrate 1102 to form one or more fluidic inlets and one or more fluidic outlets. Additionally, one or more openings may be formed to provide pathways for electrical connections to be made to both first electrode layer 1104 and second electrode layer 1108.

Figure 12:
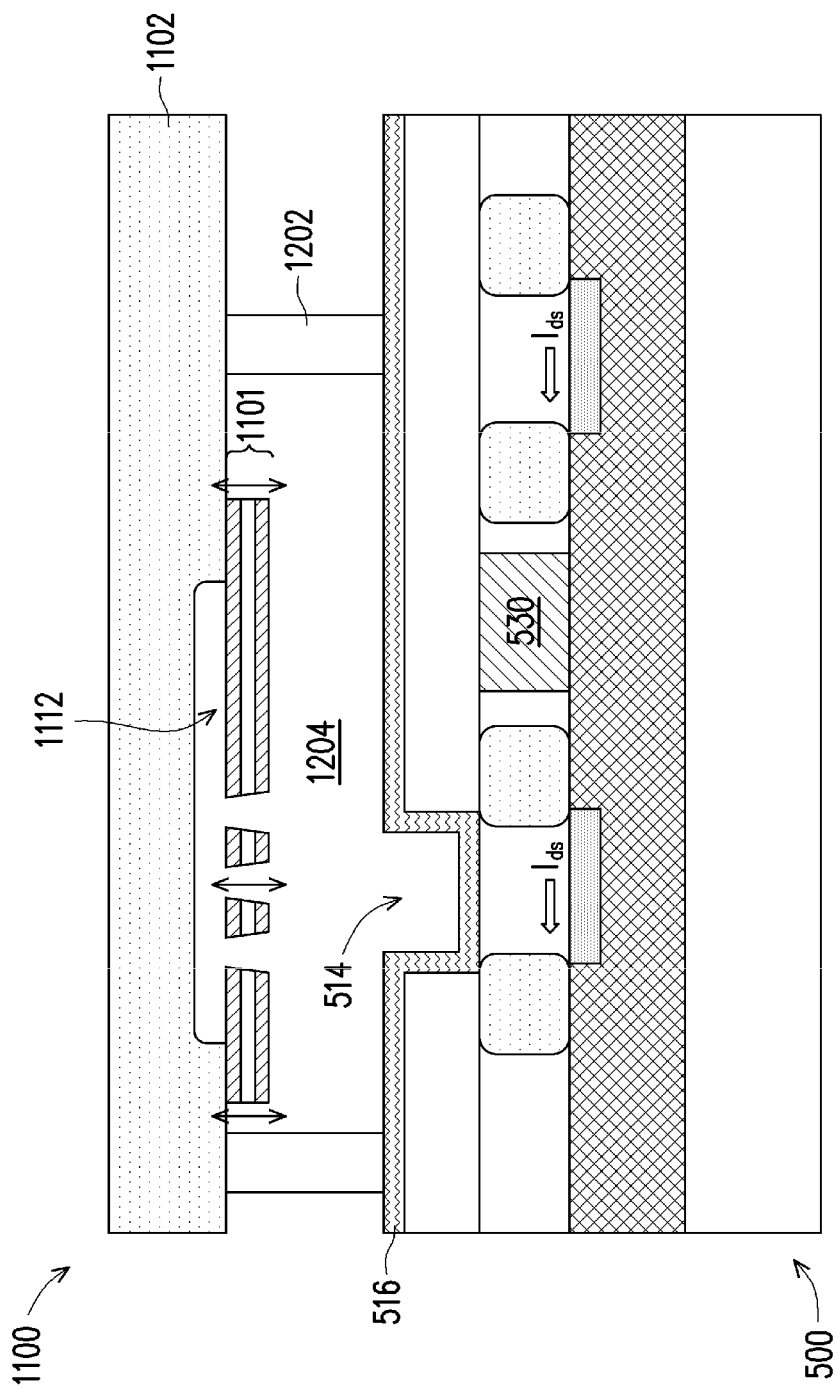
FIG. 12 illustrates the integration of a mixer with an exemplary dual gate back-side sensing FET sensor, according to some embodiments.

FIG. 12 illustrates an example integration of mixer 1100 with semiconductor device 500, according to an embodiment. Prior to the bonding of mixer 1100, channel walls 1202 may be patterned over interface layer 516 to form the walls of a microfluidic channel. Channel walls 1202 may include a dielectric material that is patterned like a photoresist using UV light, or that is dry etched. Channel walls 1202 may include a polymer that is patterned using UV light.

In some embodiments, a bonding layer is deposited first over portions of interface layer 516 to provide a better bonding surface for channel walls 1202. The bonding layer may include a dielectric material different than that of interface layer 516 such as, for example, silicon dioxide.

After channel walls 1202 have been patterned, mixer 1100 may be bonded over channel walls 1202 to form an enclosed fluidic region 1204 that defines an inner volume of the microfluidic channel. The bonding may be performed using an adhesive placed between substrate 1102 and channel walls 1202. Heat and pressure may both be applied during the bonding process to improve the bond strength. According to an embodiment, mixer 1100 is bonded such that is substantially aligned over opening 514.

Although not shown in the cross-section of FIG. 12, fluid enters into fluidic region 1204 via an opening through substrate 1102. The fluid fills fluidic region 1204, which includes opening 514 patterned over a bioFET sensor, and also fills cavity 1112 above piezoelectric stack 1101. By applying a varying electric field across the electrodes above piezoelectric stack 1101, the piezoelectric material will mechanically strain in an oscillating fashion that effectively vibrates piezoelectric stack 1101 up and down as indicated by the double ended arrows. The frequency of the vibration depends on the alternating frequency of the applied electric field, as well as the material properties of the piezoelectric film. In one example, an electric field is applied across piezoelectric stack 1101 having a DC offset between about 1 V and about 100 V with an AC component between about 10 mV peak-to-peak and about 1000 mV peak-to-peak at a frequency between about 1 kHz and about 100 kHz. The presence of cavity 1112 allows for the vertical movement of piezoelectric stack 1101 and introduces turbulence into the fluid around piezoelectric stack 1101. This fluid turbulence is also felt by the fluid around opening 514. Accordingly, the turbulence caused by mixer 1100 can increase the efficiency of the bio-reactions occurring within opening 514 above the bioFET sensor.

It should be understood that a single bioFET sensor is illustrated in FIG. 12 for clarity, but mixer 1100 may also be integrated in a similar manner over a plurality of bioFET sensors. Additionally, opening 514 may stretch across more than one of the plurality of bioFET sensors (as discussed above with reference to FIG. 7B), such that the turbulence created by mixer 1100 improves the efficiency of the bio-reactions occurring over a plurality of bioFET sensors.

In some embodiments, channel walls 1202 are replaced by portions of substrate 1102, such that substrate 1102 is directly bonded to interface layer 516. In some embodiments, the components of mixer 1100 may be recessed in substrate 1102 to form enclosed fluidic region 1204 upon bonding of substrate 1102 to interface layer 516.

Chemistry, Biology, and Interface

Figure 13:
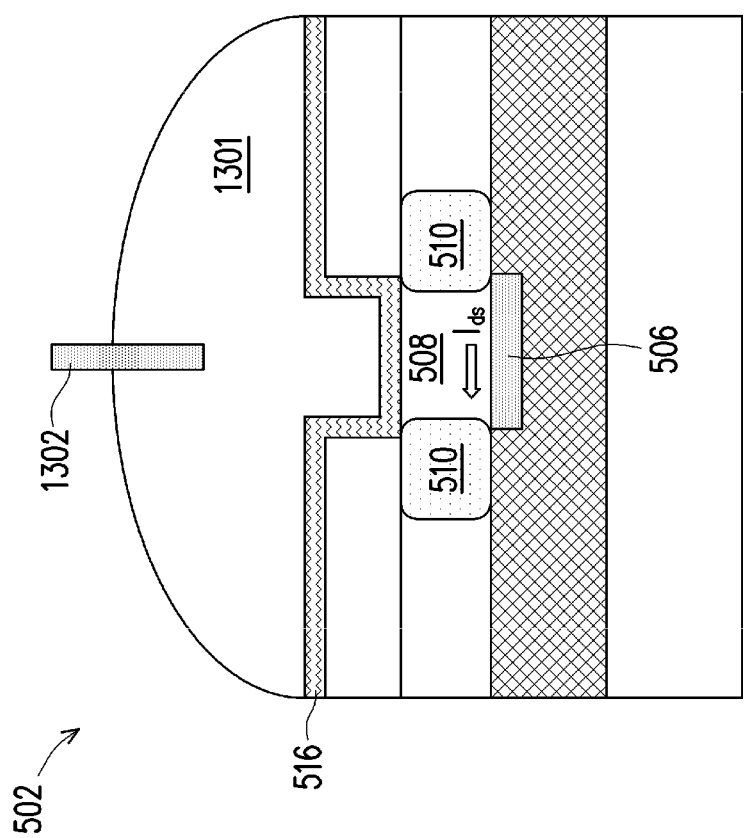
FIG. 13 illustrates a cross-sectional view of an exemplary dual gate back-side sensing FET sensor acting as a pH sensor, according to some embodiments.

An example operation of dual gate back-side FET sensor 502 as a pH sensor will now be described with reference to FIG. 13. Although the opening over dual gate back-side FET sensor 502 is illustrated in the following figures as only being over channel region 508, it should be understood that the opening may stretch further to expose other dual gate back-side FET sensors, and that the size of the opening does not change the bio-sensing operations described herein.

Briefly, a fluid gate 1302 is used to provide an electrical contact to the "back gate" of dual gate back-side FET sensor 502. A solution 1301 is provided over the reaction site of dual gate back-side FET sensor 502, and fluid gate 1302 is placed within solution 1301. The pH of the solution is generally related to the concentration of hydrogen ions [H$^+$] in the solution. The accumulation of the ions near the surface of interface layer 516 above channel region 508 affects the formation of the inversion layer within channel region 508 that forms the conductive pathway between S/D regions 510. In some embodiments, a current $I_{ds}$ flows from one S/D region to the other.

The current Is may be measured to determine the pH of solution 1301. In some embodiments, fluid gate 1302 is used as the gate of the transistor during sensing while gate 506 remains floating. In some embodiments, fluid gate 1302 is used as the gate of the transistor during sensing while gate 506 is biased at a given potential. For example, gate 506 may be biased at a potential between −2V and 2V depending on the application, while fluid gate 1302 is swept between a range of voltages. In some embodiments, fluid gate 1302 is biased at a given potential (or grounded) while gate 506 is used as the gate of the transistor (e.g., its voltage is swept across a range of potentials) during sensing. Fluid gate 1302 may be formed from platinum or may be formed from any other commonly used material(s) for reference electrodes in electrochemical analysis. An example of a reference electrode is a silver/silver chloride (Ag/AgCl) electrode, which has a stable potential value of about 0.230 V.

Figure 14B:
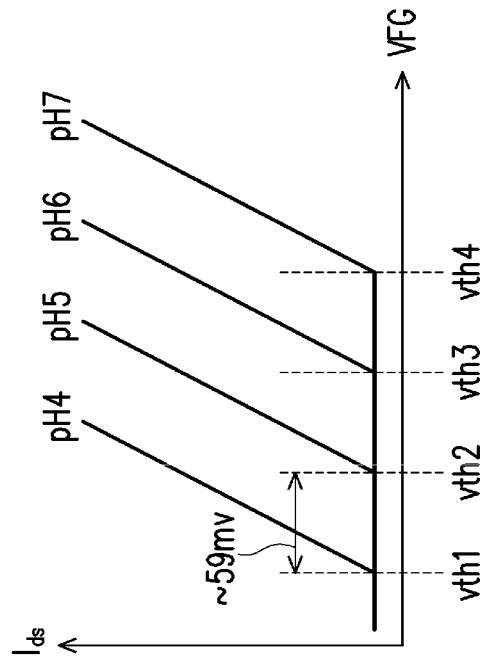
FIGS. 14A and 14B illustrate using the dual gate back-side sensing FET sensor as a pH sensor, according to some embodiments.
Figure 14A:
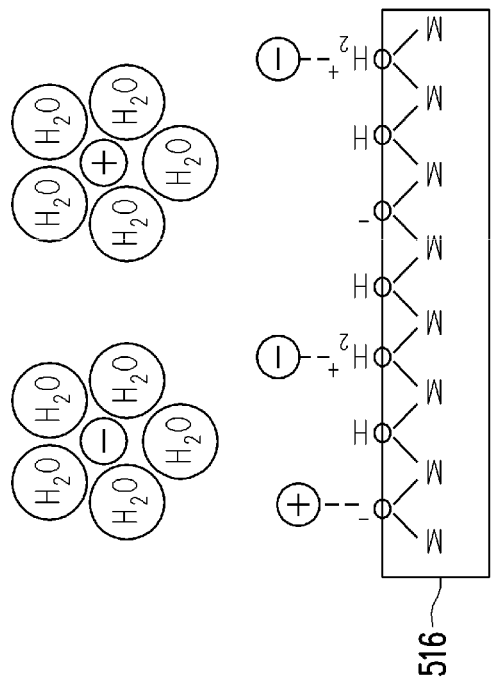

FIG. 14A shows ions in solution binding to a surface of interface layer 516. A top-most atomic layer of interface layer 516 is depicted as the various dangling [O$^-$], [OH], and [OH$_2^+$] bonds. As the ions accumulate on the surface, the total surface charge affects the threshold voltage of the transistor. As used herein, the threshold voltage is the minimum potential between the gate and the source of a FET sensor that is required to form a conductive path of minority carriers between the source and the drain of the FET sensor. The total charge also directly relates to a pH of the solution, as a higher accumulation of positive charge signifies a lower pH while a higher accumulation of negative charge signifies a higher pH.

FIG. 14B illustrates an example change in threshold voltage that results due to different pH values in an n-channel FET sensor. As can be observed in this example, a 59 mV increase in threshold voltage roughly signifies an increase of one in the pH of the solution. In other words, one pH change results in total surface charge equivalent of 59 mV when measured as the voltage required to turn ON the transistor.

Changing the threshold voltage of dual gate back-side FET sensor 502 also changes a time it takes to form a conductive path between S/D regions 510 for a given voltage input to either fluid gate 1302 or gate 506. This time delay in "turning ON" the FET sensor may be quantified using digital circuitry and used to determine an analyte concentration, according to some embodiments.

The apparatus, systems, and methods described in this application can be used to monitor interactions between various entities. These interactions include biological and chemical reactions to detect target analytes in a test sample. As an example, reactions, including physical, chemical, biochemical, or biological transformations, can be monitored to detect generation of intermediates, byproducts, products, and combinations thereof. In addition, the apparatus, systems, and methods of the present disclosure can be used to detect these reactions in various assays as described herein, including, but not limited to, circulating tumor cell assays used in liquid biopsies and chelation assays to detect the presence of heavy metals and other environmental pollutants. Such assays and reactions can be monitored in a single format or in an array format to detect, for example, multiple target analytes.

Figure 15:
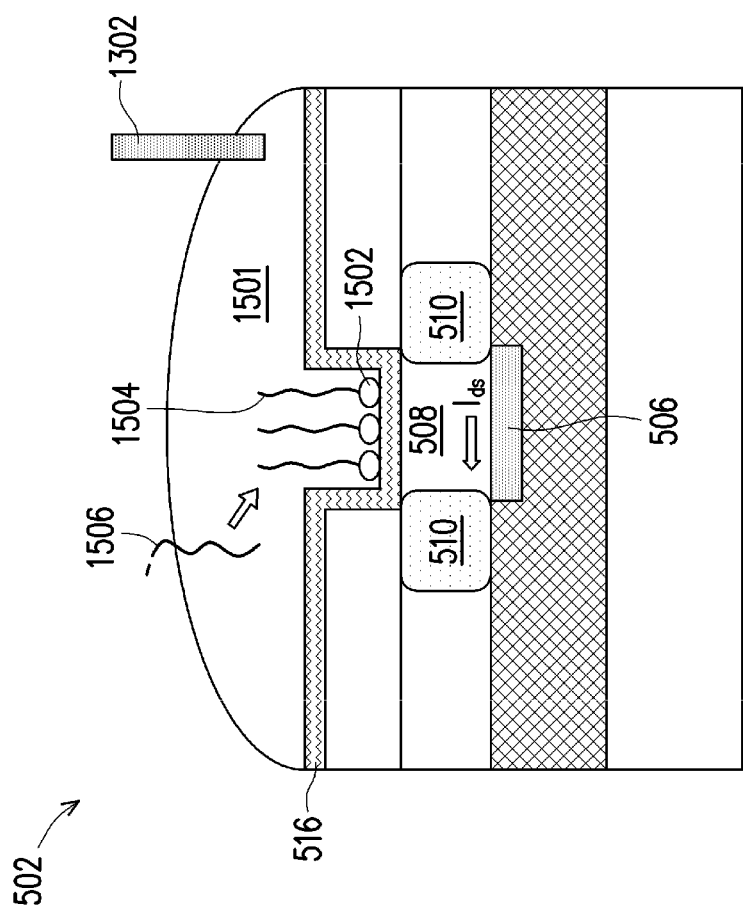
FIG. 15 illustrates a cross-sectional view of an exemplary dual gate back-side sensing bioFET detecting DNA, according to some embodiments.

Referring to FIG. 15, an example biosensing test is performed using dual gate back-side sensing FET sensor 502. Probe DNA 1504 (an example of a capture reagent) is bound to interface layer 516 via a linking molecule 1502. Linking molecule 1502 may have a reactive chemical group that binds to a portion of interface layer 516. An example of linking molecules include thiols. Linking molecules may also be formed via silanization of the surface of interface layer 516, or by exposing the surface of interface layer 516 to ammonia (NH$_3$) plasma, to form reactive NH$_2$ groups on the surface. The silanization process involves sequentially exposing the surface of interface layer 516 to different chemicals to build up covalently-bound molecules on the surface of interface layer 516, as would be generally understood by a person skilled in the relevant art. Probe DNA 1504 represents single stranded DNA. Dual gate back-side sensing FET sensor 502 illustrated in FIG. 15 is one bioFET sensor within a sensor array that would exist on a chip, according to some embodiments.

Probe DNA 1504 may be immobilized on interface layer 516 prior to subjecting the FET sensor to fluid sample 1501. Fluid sample 1501 may include the matching single stranded DNA sequence 1506 that binds strongly to its matching probe DNA 1504. The binding of additional DNA increases the negative charge present on interface layer 516 and directly above channel region 508 of the FET sensor.

Figure 16B:
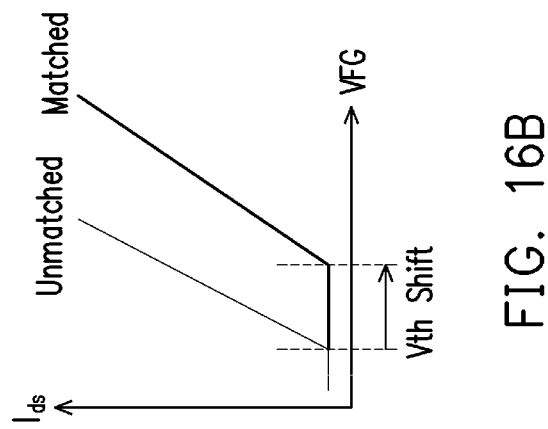
FIG. 16B illustrates a change in threshold voltage for an exemplary dual gate back-side sensing bioFET based on matched analyte binding, according to some embodiments.
Figure 16A:
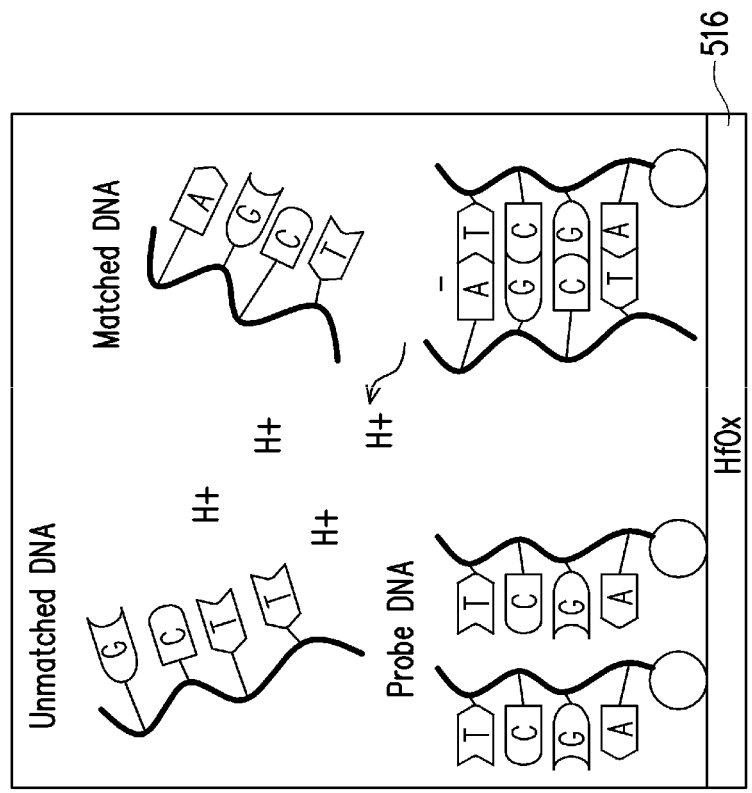
FIG. 16A illustrates binding mechanics of DNA on a receptor surface, according to some embodiments.

The DNA binding is illustrated conceptually in FIG. 16A. Here, probe DNA having nucleic acid sequence TCGA binds to its complementary matched strand having nucleic acid sequence AGCT. Any unmatched sequences does not hybridize with the probe DNA sequences. The binding of the matching DNA increases the negative charge built up at the interface of interface layer 516. In the example illustrated in FIG. 16A, interface layer 516 is hafnium oxide.

FIG. 16B illustrates a shift in the threshold voltage of the dual gate back-side sensing FET sensor when matching DNA is bound to the surface of interface layer 516. Briefly, voltage may be applied to fluid gate 1302 until the FET sensor "turns on" and current flows between S/D regions 510. In another example, voltage is applied to gate 506 to turn ON the FET sensor while fluid gate 1302 is biased at a given potential. When more negative charge is present at interface layer 516 due to complementary DNA binding, a higher voltage is required to form the conductive inversion layer within channel region 508. Thus, according to some embodiments, a higher voltage may be applied to fluid gate 1302, or gate 506, before the FET sensor conducts and $I_{ds}$ current flows. This difference in threshold voltage may be measured and used to determine not only the presence of the target matching DNA sequence, but also its concentration. It should be understood that a net positive accumulated charge at interface layer 516 would cause the threshold voltage to decrease rather than increase. Additionally, the change in threshold voltage will have the opposite sign for an n-channel FET as compared to a p-channel FET.

Figure 17:
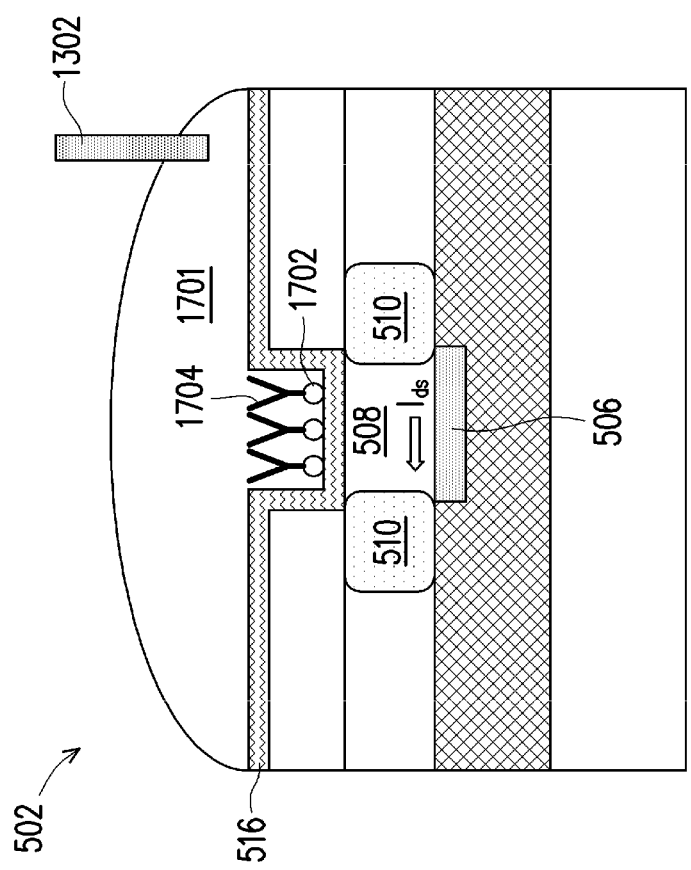
FIG. 17 illustrates a cross-sectional view of an exemplary dual gate back-side sensing bioFET having antibodies immobilized on its sensing layer, according to some embodiments.

Referring to FIG. 17, another example biosensing test is performed using dual gate back-side FET sensor 502. Probe antibodies 1704 (another example of capture reagents) are bound to interface layer 516 via linking molecules 1702. Linking molecules 1702 may have a reactive chemical group that binds to a portion of interface layer 516. A sample solution 1701 may be provided over probe antibodies 1704 to determine if the matching antigens are present within sample solution 1701.

Figure 18:
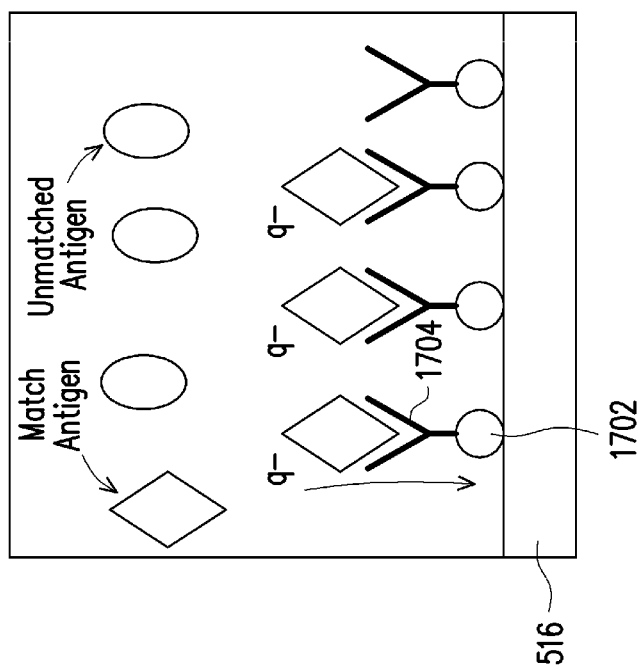
FIG. 18 illustrates binding mechanics of antigens and antibodies on a receptor surface, according to some embodiments.

Referring to FIG. 18, the binding process of matching antigens to probe antibodies 1704 is illustrated. Here, matching antigens will bind to the immobilized probe antibodies while unmatched antigens will not bind. Similar to the DNA hybridization process described above, the matching antigens will change the accumulated charge present at interface layer 516. The shift in threshold voltage due to the accumulated charge from matching antigens binding to the probe antibodies is measured in substantially the same way as discussed above with reference to FIG. 16B.

FINAL REMARKS

Described herein are embodiments of a bioFET device that includes a common opening over a plurality of dual gate back-side FET sensors. According to some embodiments, a bioFET device includes a semiconductor substrate having a first surface and an opposite, parallel second surface and a plurality of bioFET sensors on the semiconductor substrate. Each of the bioFET sensors includes a gate structure formed on the first surface of the semiconductor substrate and a channel region formed within the semiconductor substrate beneath the gate structure and between source/drain (S/D) regions in the semiconductor substrate. The channel region includes a portion of the second surface of the semiconductor substrate. The bioFET device also includes an isolation layer disposed on the second surface of the semiconductor substrate. The isolation layer has an opening that is positioned over the channel region of more than one bioFET sensor of the plurality of bioFET sensors. The bioFET device also includes an interface layer disposed on the channel region of the more than one bioFET sensor in the opening.

According to some embodiments, a method of fabricating a bioFET device includes forming a plurality of gates on a first surface of a semiconductor substrate, where each of the plurality of gates is formed over a corresponding channel region in the semiconductor substrate. The method also includes forming S/D regions in the semiconductor substrate on either side of each channel region. The method also includes forming an opening in an isolation layer on a second surface of the semiconductor substrate, the second surface being opposite and parallel to the first surface of a semiconductor substrate. Each of the channel regions in the substrate includes a portion of the second surface of the semiconductor substrate, and the opening exposes a portion of the second surface of the semiconductor substrate that includes more than one channel region. The method includes disposing an interface layer on the second surface of the semiconductor substrate within the opening.

According to some embodiments, a sensor array includes a semiconductor substrate having a first surface and an opposite, parallel second surface, and a plurality of bioFET sensors arranged in a matrix of rows and columns on the semiconductor substrate. Each of the bioFET sensors includes a gate formed on the first surface of the semiconductor substrate and a channel region formed within the semiconductor substrate beneath the gate and between S/D regions in the semiconductor substrate. The channel region includes a portion of the second surface of the semiconductor substrate. The sensor array also includes an isolation layer disposed on the second surface of the semiconductor substrate and having an opening that extends along a length of at least one row of the matrix of rows such that the opening is positioned over the channel region of more than one bioFET sensor of the plurality of bioFET sensors in the at least one row. The sensor array also includes an interface layer disposed on the second surface of the semiconductor substrate within the opening.

It is to be appreciated that the Detailed Description section, and not the Abstract of the Disclosure section, is intended to be used to interpret the claims. The Abstract of the Disclosure section may set forth one or more but not all exemplary embodiments of the present disclosure as contemplated by the inventor(s), and thus, is not intended to limit the present disclosure and the subjoined claims in any way.

It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments but should be defined in accordance with the subjoined claims and their equivalents.

What is claimed is:

1. A bio-field effect transistor (bioFET) device, comprising:
    a semiconductor substrate having a first surface and an opposite, parallel second surface;
    a plurality of bioFET sensors disposed on the semiconductor substrate, each bioFET sensor comprising:
        a gate formed on the first surface of the semiconductor substrate; and
        a first channel region formed within the semiconductor substrate beneath the gate and between a first pair of source/drain (S/D) regions in the semiconductor substrate, wherein the first channel region includes a first portion of the second surface of the semiconductor substrate;
    a plurality of access FETs, each of the access FETs having an access gate disposed on the first surface of the semiconductor substrate and a second channel region formed within the semiconductor substrate beneath the access gate and between a second pair of S/D regions in the semiconductor substrate, wherein the second channel region includes a second portion of the second surface of the semiconductor substrate;

an isolation layer disposed on the second surface of the semiconductor substrate, wherein the isolation layer extends over the second channel regions of the plurality of access FETs and wherein the isolation layer has an opening positioned over the first channel region of more than one bioFET sensor of the plurality of bioFET sensors; and a continuous interface layer disposed on the isolation layer and within the opening over the first channel region of the more than one bioFET sensor, wherein the continuous interface layer extends over the second channel regions of the plurality of access FETs.

2. The bioFET device of claim 1, further comprising a microfluidic channel disposed over the plurality of access FETs and the plurality of bioFET sensors.

3. The bioFET device of claim 1, wherein one of the first pair of S/D regions of each of the plurality of bioFET sensors is electrically coupled to one of the second pair of S/D regions of the plurality of access FETs.

4. The bioFET device of claim 1, further comprising a piezoelectric mixer disposed over the plurality of access FETs and over the plurality of bioFET sensors, wherein the piezoelectric mixer is bonded to the continuous interface layer through channel walls disposed on the plurality of access FETs and the plurality of bioFET sensors.

5. The bioFET device of claim 1, wherein each bioFET sensor further comprises:
a second gate formed on the first surface of the semiconductor substrate; and
a third channel region formed within the semiconductor substrate beneath the second gate and between the first pair of S/D regions in the semiconductor substrate.

6. A bio-field effect transistor (bioFET) device, comprising:
a semiconductor substrate having a first surface and an opposite, parallel second surface;
a plurality of bioFET sensors disposed on the semiconductor substrate, each bioFET sensor comprising:
a sensing gate formed on the second surface of the semiconductor substrate;
first and second gates formed on the first surface of the semiconductor substrate; and
first and second channel regions formed within the semiconductor substrate beneath the first and second gates, respectively, wherein the first and second channel regions include first and second portions, respectively, of the second surface of the semiconductor substrate;
a common source/drain (S/D) region disposed between the first and second channel regions; and
another S/D region coupled to a ground potential;
a plurality of access FETs, each of the access FETs having an access gate disposed on the first surface of the semiconductor substrate and a third channel region formed within the semiconductor substrate beneath the access gate, wherein the third channel region includes a third portion of the second surface of the semiconductor substrate;
an isolation layer disposed on the second surface of the semiconductor substrate, the isolation layer having an opening positioned over the first and second channel regions of more than one bioFET sensor of the plurality of bioFET sensors;
a first portion of an interface layer disposed within the opening on the first and second channel regions of the more than one bioFET sensor and a second portion of the interface layer disposed on the plurality of access FETs; and
a microfluidic channel positioned over the plurality of access FETs and the plurality of bioFET sensors and configured to deliver fluid into the opening through the isolation layer.

7. The bioFET device of claim 6, wherein an S/D region of each access FET of the plurality of access FETs is electrically coupled to the common S/D region of each bioFET sensor of the plurality of bioFET sensors.

8. The bioFET device of claim 6, wherein the microfluidic channel comprises a piezoelectric mixer aligned substantially over the opening through the isolation layer.

9. The bioFET device of claim 6, wherein each bioFET sensor further comprises:
a fourth channel region formed within the semiconductor substrate beneath the sensing gate.

10. The bioFET device of claim 6, wherein the opening has a longest length aligned with an X-direction and the microfluidic channel is configured to deliver fluid that flows over the opening in the X-direction.

11. A sensor array, comprising:
a semiconductor substrate having a first surface and an opposite, parallel second surface;
a plurality of bioFET sensors arranged in a matrix of rows and columns on the semiconductor substrate, each bioFET sensor comprising:
a sensing gate formed on the second surface of the semiconductor substrate;
first and second gates formed on the first surface of the semiconductor substrate; and
first and second channel regions formed within the semiconductor substrate beneath first and second gates, respectively, wherein the first and second channel regions include first and second portions, respectively, of the second surface of the semiconductor substrate;
a common source/drain (S/D) region disposed between the first and second channel regions; and
another S/D region coupled to a ground potential;
a plurality of access FETs, each of the access FETs having an access gate disposed on the first surface of the semiconductor substrate and a third channel region formed within the semiconductor substrate beneath the access gate, wherein the third channel region includes a third portion of the second surface of the semiconductor substrate;
an isolation layer disposed on the second surface of the semiconductor substrate, the isolation layer having an opening that extends along a length of at least one row of the matrix of rows such that the opening extends over the first and second channel regions of more than one bioFET sensor of the plurality of bioFET sensors in the at least one row; and
a continuous interface layer disposed on the isolation layer and on the second surface of the semiconductor substrate exposed within the opening over the first and second channel regions.

12. The sensor array of claim 11, wherein the plurality of access FETs are arranged in a row on the semiconductor substrate, and wherein the opening in the isolation layer is not positioned over the third channel regions of the plurality of access FETs.

13. The sensor array of claim 11, wherein the common S/D region of each bioFET sensor of the plurality of bioFET sensors is electrically coupled to an S/D region of a corresponding access FET of the plurality of access FETs.

14. The sensor array of claim 13, wherein the corresponding access FET is arranged on the semiconductor substrate to be adjacent to at least one bioFET sensor.

15. The sensor array of claim 11, further comprising a piezoelectric mixer bonded over the opening through the isolation layer.

16. A sensor array, comprising:
a semiconductor substrate having a first surface and an opposite, parallel second surface;
a plurality of bioFET sensors arranged in a matrix of rows and columns on the semiconductor substrate, each bioFET sensor comprising:
a gate formed on the first surface of the semiconductor substrate; and
a first channel region formed within the semiconductor substrate beneath the gate and between a first pair of source/drain (S/D) regions in the semiconductor substrate, wherein the channel region includes a first portion of the second surface of the semiconductor substrate;
a plurality of access FETs, each of the access FETs having an access gate disposed on the first surface of the semiconductor substrate and a second channel region formed within the semiconductor substrate beneath the access gate, wherein the second channel region includes a second portion of the second surface of the semiconductor substrate;
an isolation layer disposed on the second surface of the semiconductor substrate, wherein the isolation layer extends over the second channel regions of the plurality of access FETs and wherein the isolation layer has an opening that extends along a length of at least one row of the matrix of rows such that the opening is positioned over the first channel region of more than one bioFET sensor of the plurality of bioFET sensors in the at least one row;
an interface layer disposed on the second surface of the semiconductor substrate within the opening and on the second channel regions of the plurality of access FETs; and
a microfluidic channel positioned over the plurality of access FETs and the plurality of bioFET sensors and configured to deliver fluid into the opening in the isolation layer.

17. The sensor array of claim 16, further comprising a piezoelectric mixer disposed over the plurality of access FETs and over the plurality of bioFET sensors, wherein the piezoelectric mixer is bonded to the interface layer through channel walls disposed on the plurality of access FETs and the plurality of bioFET sensors.

18. The sensor array of claim 16, further comprising a piezoelectric mixer bonded over the opening through the isolation layer.

19. The sensor array of claim 16, wherein the opening has a longest length aligned with an X-direction and the microfluidic channel is configured to deliver fluid that flows over the opening in the X-direction.

20. The sensor array of claim 19, wherein the opening spans along a Y-direction such that the opening is also positioned over the channel region of more than one bioFET sensor of the plurality of bioFET sensors in one or more other rows.

21. A bioFET device, comprising:
a semiconductor substrate having a first surface and an opposite, parallel second surface;
an access transistor having an access gate disposed on the first surface of the semiconductor substrate and a first channel region formed within the semiconductor substrate beneath the access gate;
a shunt transistor having a shunt gate disposed on the first surface of the semiconductor substrate and a second channel region formed within the semiconductor substrate beneath the shunt gate, wherein the access gate and the shunt gate share a first common source/drain (S/D) region disposed between the first and second channel regions;
a bioFET sensor having first and second gates disposed on the first surface of the semiconductor substrate and a sensing gate disposed on the second surface of the semiconductor substrate, wherein the first and second gates share a second common S/D region disposed between third and fourth channel regions formed within the semiconductor substrate beneath the first and second gates, respectively,
wherein the access and shunt transistors are disposed adjacent to each other and the bioFET sensor is disposed opposite to the access and shunt transistors;
an isolation layer disposed on the second surface of the semiconductor substrate, wherein the isolation layer has an opening that exposes a portion of the second surface of the semiconductor substrate that includes the third and fourth channel regions; and
an interface layer disposed on the second surface of the semiconductor substrate within the opening.

22. The bioFET device of claim 21, further comprising a piezoelectric mixer disposed on the interface layer.

23. The bioFET device of claim 21, further comprising a piezoelectric mixer disposed over the opening through the isolation layer.

24. The bioFET device of claim 21, further comprising a piezoelectric mixer configured to form an enclosed fluidic region over the opening.

25. The bioFET device of claim 21, wherein the first common S/D region is electrically coupled to the second common S/D region.

26. A bioFET device, comprising:
an array of access transistors and shunt transistors, wherein the access and shunt transistors are arranged in an alternating configuration in the array,
wherein each of the access transistors have an access gate disposed on a first surface of a semiconductor substrate and a first channel region formed within the semiconductor substrate beneath the access gate, and
wherein each of the shunt transistors have a shunt gate disposed on the first surface of the semiconductor substrate and a second channel region formed within the semiconductor substrate beneath the shunt gate, wherein the access gate and the shunt gate share a common source/drain (S/D) region disposed between the first and second channel regions;
an array of bioFET sensors, wherein each of the bioFET sensors have a gate disposed on the first surface of the semiconductor substrate and S/D regions disposed on either side of a third channel region formed within the semiconductor substrate beneath the gate, wherein the array of bioFET sensors and the array of access and shunt transistors are disposed on different portions of a semiconductor substrate;

an isolation layer disposed on the second surface of the semiconductor substrate, wherein the isolation layer has an opening that exposes a portion of the second surface of the semiconductor substrate that includes the third channel region;

an interface layer disposed on the second surface of the semiconductor substrate within the opening; and a microfluidic channel disposed on the interface layer.

27. The bioFET device of claim 26, further comprising a piezoelectric mixer bonded to the microfluidic channel.

28. The bioFET device of claim 27, wherein the piezoelectric mixer comprises a piezoelectric film stack suspended within the microfluidic channel.

29. The bioFET device of claim 26, wherein the opening has a longest length aligned with an X-direction and the microfluidic channel delivers fluid that flows over the opening in the X-direction.

30. The bioFET device of claim 26, wherein the common S/D region is electrically coupled to one of the S/D regions of the bioFET sensor.

* * * * *